United States Patent
Al Ahmad et al.

(10) Patent No.: US 11,033,195 B2
(45) Date of Patent: Jun. 15, 2021

(54) PIEZOELECTRIC RELATED APPARATUS AND METHOD FOR EXTRACTING CARDIAC CYCLE FEATURES FROM RESPIRATION SIGNALS

(71) Applicant: United Arab Emirates University, Al Ain (AE)

(72) Inventors: Mahmoud F. Y. Al Ahmad, Al Ain (AE); Areen Abdallah Romi Allataifeh, Al Ain (AE)

(73) Assignee: United Arab Emirates University, Al Ain (AE)

( * ) Notice: Subject to any disclaimer, the term of this patent is extended or adjusted under 35 U.S.C. 154(b) by 473 days.

(21) Appl. No.: 15/890,000

(22) Filed: Feb. 6, 2018

(65) Prior Publication Data
US 2018/0214034 A1    Aug. 2, 2018

Related U.S. Application Data

(63) Continuation-in-part of application No. 15/095,956, filed on Apr. 11, 2016, now Pat. No. 10,722,124.
(Continued)

(51) Int. Cl.
*A61B 5/0245*    (2006.01)
*A61B 5/021*    (2006.01)
(Continued)

(52) U.S. Cl.
CPC ............ *A61B 5/0245* (2013.01); *A61B 5/021* (2013.01); *A61B 5/029* (2013.01);
(Continued)

(58) Field of Classification Search
None
See application file for complete search history.

(56) References Cited

U.S. PATENT DOCUMENTS

| | | | |
|---|---|---|---|
| 4,884,578 A | 12/1989 | Morgenstern | |
| 6,535,754 B2 * | 3/2003 | Fishbein | A61B 5/055 600/411 |

(Continued)

FOREIGN PATENT DOCUMENTS

| | | |
|---|---|---|
| WO | 2013/179189 A1 | 12/2013 |
| WO | 2017079878 A1 | 5/2017 |

OTHER PUBLICATIONS

Joonas Paalasmaa et al., "Unobtrusive Online Monitoring of Sleep at Home," Conference proceedings: Annual International Conference of the IEEE Engineering in Medicine and Biology Society, Aug. 2012, 6 pgs.
(Continued)

*Primary Examiner* — Michael R Bloch
(74) *Attorney, Agent, or Firm* — Fitch, Even, Tabin & Flannery LLP

(57) ABSTRACT

A method and system for extracting cardiac cycle parameters from a respiration signal is disclosed. The technique comprises an array of piezoelectric sensors planted on the chest. The chest membrane exhibits the characteristics of bulky attenuator with certain time delay. Contractions and expansions of the heart and lungs muscles model a mechanical load and produce a relative induced strain on the piezoelectric sheet which in turn causes the piezoelectric material to generate a corresponding conformal voltage signal that is mapped with the heart actions. The resultant voltage signal is therefore used to extract and model the corresponding heart parameters utilizing piezoelectric as well as signal processing theories. a direct relationship is established between the output voltage produced by the piezoelectric transducer under hold breathing and the respiration signal collected by the same transducer with respiration.

19 Claims, 18 Drawing Sheets

Related U.S. Application Data

(60) Provisional application No. 62/253,496, filed on Nov. 10, 2015.

(51) Int. Cl.
| | |
|---|---|
| *A61B 5/029* | (2006.01) |
| *A61B 7/04* | (2006.01) |
| *A61B 5/11* | (2006.01) |
| *A61B 5/00* | (2006.01) |
| *A61B 5/024* | (2006.01) |
| *A61B 5/08* | (2006.01) |
| *A61B 5/113* | (2006.01) |
| *A61B 5/0205* | (2006.01) |

(52) U.S. Cl.
CPC ........ *A61B 5/02438* (2013.01); *A61B 5/0816* (2013.01); *A61B 5/1102* (2013.01); *A61B 5/113* (2013.01); *A61B 5/7275* (2013.01); *A61B 7/04* (2013.01); *A61B 5/002* (2013.01); *A61B 5/0205* (2013.01); *A61B 5/6823* (2013.01); *A61B 5/7246* (2013.01); *A61B 5/7253* (2013.01); *A61B 5/7257* (2013.01)

(56) References Cited

U.S. PATENT DOCUMENTS

| | | | | |
|---|---|---|---|---|
| 2008/0154144 | A1* | 6/2008 | Unver | A61B 5/02028 600/528 |
| 2011/0021928 | A1* | 1/2011 | Giovangrandi | A61B 5/0205 600/484 |
| 2017/0127951 | A1 | 5/2017 | Al Ahmad | |

OTHER PUBLICATIONS

Antonio Lanata et al., "A Multimodal Transducer for Cardiopulmonary Activity Monitoring in Emergency," IEEE Transactions on Information Technology in Biomedicine, vol. 14, No. 3, May 2010, pp. 817-825.

Shinichi Sato et al., "System for simultaneously monitoring heart and breathing rate in mice using a piezoelectric transducer," Med & Biol Engineering &Computing, (2006) 44, pp. 353-362.

International Search Report and Written Opinion, dated May 6, 2019 for International Application No. PCT/IB2019/050929 (10 pgs).

James A. C. Patterson et al., "A Flexible, Low Noise Reflective PPG Sensor Platform for Ear-Worn Heart Rate Monitoring," IEEE Computer Society, Body Sensor Networks, 286-291 (2009).

So-Hyun Jansen-Park et al., "A monitoring and physiological control system for determining aortic valve closing with a ventricular assist device," European Journal of Cardio-Thoracic Surgery Advance Access, published Feb. 4, 2014, 1-5.

Sunghyun Yoon et al., "A Skin-attachable Flexible Piezoelectric Pulse Wave Energy Harvester," Journal of Physics: Conference Series 557 (2014).

N. Al Taradeh et al., "Non-invasive piezoelectric detection of heartbeat rate and blood pressure," Electronics Letters, Mar. 19, 2015, vol. 51, No. 6, pp. 452-454.

Marta Carrara et al., "Classification of Cardiac Rhythm Based on Heart Rate Dynamics," 8th Conference of the European Study Group on Cardiovascular Oscillations, 91-92 (2014).

M.M.A. Hashem et al., "Design and Development of a Heart Rate Measuring Device using Fingertip," International Conference on Computer and Communication Engineering, (2010), May 11-13, 2010, Kuala Lumpur, Malaysia.

J M Deibele, "Dynamic separation of pulmonary and cardiac changes in electrical impedance tomography," Physiol. Meas., 29 (2008) S1-S14.

Dilpreet Buxi et al., "Early Results on Wrist Based Heart Rate Monitoring using Mechanical Transducers," 32nd Annual International Conference of the IEEE EMBS, Buenos Aires, Argentina, Aug. 31 to Sep. 4, 2010, 4407-4410.

A Vehkaoja et al., "Extracting the respiration cycle lengths from ECG signal recorded with bed sheet electrodes," Journal of Physics: Conference Series 459 (2013).

T. Rahman, "Extraction of cardiac and respiration signals in electrical impedance tomography based on independent component analysis," J Electr Bioimp, vol. 4, pp. 38-44, 2013.

Jeong Su Lee et al., "Flexible Capacitive Electrodes for Minimizing Motion Artifacts in Ambulatory Electrocardiograms," Sensors, 14: 14732-14743 (2014).

You Min Chang et al., "Heartbeat Monitoring Technique Based on Corona-Poled PVDF Film Sensor for Smart Apparel Application," Solid State Phenomena, vols. 124-126 (2007) pp. 299-302.

Abraham et al., "Impact of Introduction of Pulmonary Artery Pressure Monitoring for Heart Failure Management: Longitudinal Results from the CHAMPION Trial," JACC, Apr. 1, 2014, vol. 63, Issue 12.

Kiyotaka Ho et al., "Multi Sensor Approach to Detection of Heartbeat and Respiratory Rate Aided by Fuzzy Logic," IEEEE, 2010, pp. 1-6.

Massimilian Pieraccini et al., "Detection of Breathing and Heartbeat Through Snow Using a Microwave Transceiver," IEEE Geoscience and Remote Sensing Letters, vol. 5, No. 1, Jan. 2008.

Mahmoud Al Ahmad, "Piezoelectric extraction of ECG signal," Scientific Reports, Nov. 17, 2016, 7 pages.

P. Piskulak et al., "Computer Program for Automatic Identification of Artifacts in Impedance Cardiography Signals Recorded during Ambulatory Hemodynamic Monitoring," XIII Mediterranean Conference on Medical and Biological Engineering and Computing, 2013, 766-769.

Xiufeng Yang et al., "Textile Fiber Optic Microbend Sensor Used for Heartbeat and Respiration Monitoring," IEEE Sensors Journal, vol. 15, No. 2, Feb. 2015, 757-761.

David D. McManus et al., Abstract 319: "Transthoracic Bioimpedance Monitoring Predicts Heart Failure Decompensation and Early Readmission after Heart Failure Hospitalization: Preliminary Data from SENTINEL-HF," Circulation: Cardiovascular Quality and Outcomes, 2014; 7:A319.

Tal Klap et al., "Using Piezoelectric Sensor for Continuous-Contract-Free Monitoring of HEart and Respiration Rates in Real-Life Hospital Settings," Computing in Cardiology, 2013; 40: 671-674.

\* cited by examiner

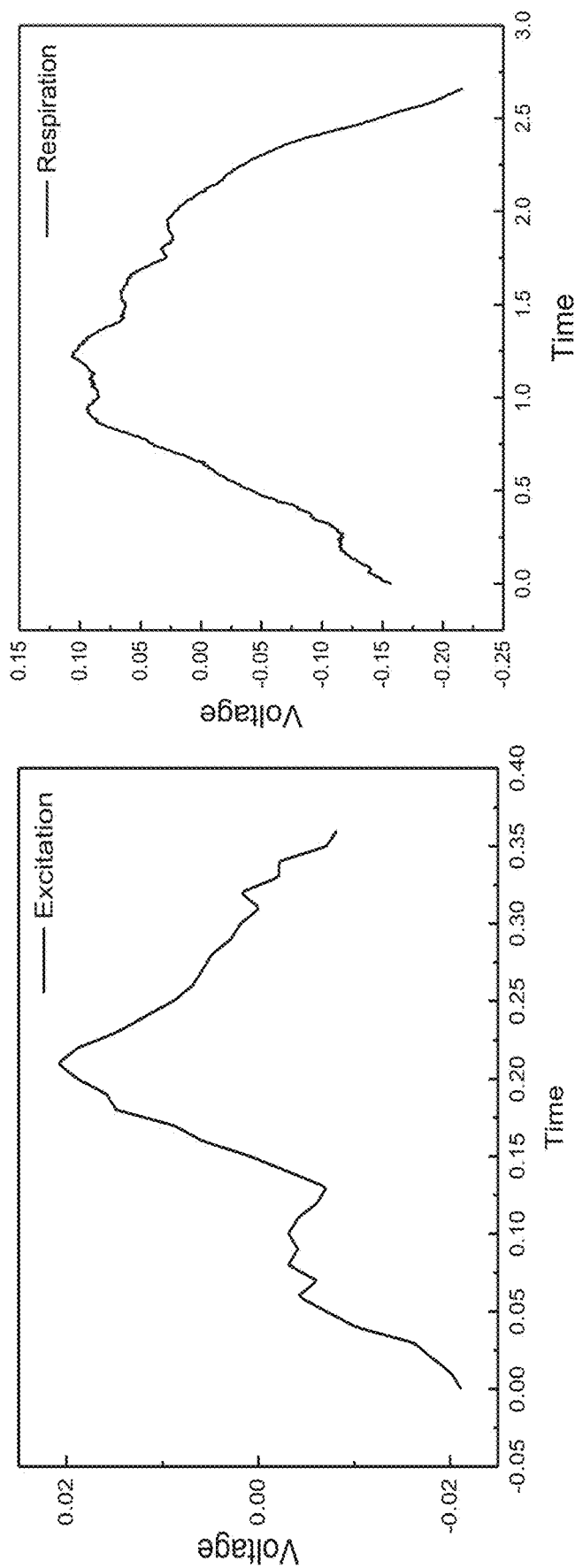

PIEZOELECTRIC RELATED APPARATUS AND METHOD FOR EXTRACTING CARDIAC CYCLE FEATURES FROM RESPIRATION SIGNALS

CROSS-REFERENCE TO RELATED APPLICATIONS

This application is a continuation-in-part application of U.S. application Ser. No. 15/095,956, filed on Apr. 11, 2016, entitled "Apparatus and Method for Physiological Mechanical and Electrical Activity Monitoring," which claims the benefit of Provisional Application No. 62/253,496, filed on Nov. 10, 2015, entitled "Apparatus and Method for Cardiac Mechanical Activity Monitoring," the entire disclosures of which are incorporated herein by reference.

TECHNICAL FIELD

This invention relates generally to monitoring of cardiac mechanical and electrical activity and more particularly to extracting cardiac cycle features from respiration signals using solely piezoelectric material and signal processing techniques.

BACKGROUND

Monitoring of the heart's mechanical and electrical dynamics and its immediate periphery is essential to fully characterise and understand its functionality and variations. The monitoring and early detection of any abnormalities or variations in the cardiac cycle functionality are very critical and have significant impact on the prevention of disease and associated complications. Heartbeat rate and blood pressure are two heart parameters that are fundamental for the prediction of any heart abnormalities. Other cardiac parameters may also be used.

Attention has been focused on assessing the biophysical properties of the heart's components using traditional equipment and monitors. One example is phtoplethysmography (PPGG) sensors. This device operates by observing the effect of blood engorgement and composition on light absorption during systole phase. Another example is the electrocardiogram (ECG) device that has a capacitive electrode with a shield over conductive foam. Although ECG devices are commercialized, their use is inconvenient for long-term usage. These traditional techniques are time consuming because of the need for installing multiple probes on the subject to obtain reliable measurements. They also require expensive, bulky and not easily accessible equipment. Furthermore, such equipment allow for the monitoring of the cardiac parameters only when the subject is in proximity to the dedicated equipment.

Piezoelectric transducers have also been used to identify, isolate and measure cardiac activity. Many researchers have developed techniques to capture the cardiac cycle corresponding signals and separate it from noises as well as from other important vital signs such as respiration. T. Rahman et al., "Extraction of cardiac and respiration signals in electrical impedance tomography based on independent component analysis", J Electr Bioimp, vol. 4, pages 38-44, 2013 have implemented an independent component analysis (ICA) in the electrical impedance tomography (EIT) to separate the cardiac and respiration signals from each other. Experiments were implemented using a 16 channel EIT device; the electrodes of the channels were placed around the thorax circumferentially. It was performed for only 40s and not designed for continuous monitoring. The setup described by the author suggests that the system is uncomfortable to use for a prolonged period of time.

US Patent Application No. U.S. Pat. No. 4,884,578A describes an apparatus for monitoring respiration and cardiac activity of a person lying in a bed mounted for poly-directional movement and subjected to a restoring force when the bed is disturbed from its normal position. Pulses originating from the person are detected by a vertically oriented sensor and a pair of horizontally oriented sensors thereby permitting monitoring of a wide range of respiratory and cardiac activity. The ballistic effect is measured by sensors, which may be piezoelectric sensors. To free the subject of any obtrusions, the sensors are described to be attached to or embedded into the bed. Because of the positioning of the body on the bed, the orientation of the sensors is important to properly detect the signals resulting from the cardiac and respiratory actions of the subject lying on the bed.

Another example of the use of piezoelectric sensors to monitor cardiac and respiratory activity may be found in International Applicant No. WO 2013179189A1. This application describes an apparatus and method for separating cardiac and respiratory signals from vital signals. Piezoelectric sensors are coupled to a surface of a supporting system, such as a bed. When the subject rests on the bed, a set of sensors are positioned in one orientation to detect movement of the bed that is the result of the expansion of the subject's body during the breathing action. Another set of sensors are position in an orientation to detect movement on the bed that is the result of the ballistic effect of cardiac activity of the subject.

The inventions taught in these systems require the electrodes to be placed in a certain orientation. Further, the systems require the subject to be in proximity of the device containing the piezoelectric electrodes and the system are taught to be stationary such that free movement of the subject is limited while using the devices.

There is a desire in the field for continuous and real-time monitoring capabilities using easily accessible contactless probing systems and the development of techniques to identify, isolate from other physiological activities and measure a wide range of cardiac cycle parameters effectively, passively, non-invasively, without the need to restrict or limit the subject's movement and also without the need for the subject to carry with him equipment that may disrupt his daily routine.

SUMMARY

The foregoing is a summary and contains simplifications, generalization, and omissions of detail. Those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of any subject matter described herein.

The invention has several aspects. One aspect provides for a method of determining cardiac or lungs activity of a subject based on monitoring respiration activity of the subject solely by using at least one piezoelectric sensor coupled to a body part of the subject. The method includes:

obtaining a first piezoelectric electrical signal from the at least one piezoelectric sensor. The first piezoelectric electrical signal is based on mechanical movement of the body part related to a breathing activity of the subject during a first period and a hold respiration activity of the subject during a second period different from the first period. The breathing activity and the hold breathing activity are performed under a set of conditions. The method also includes obtaining a second piezoelectric electrical signal from the at least one piezoelectric sensor. The second piezoelectric electrical signal is based on mechanical movement of the body part related to respiration activity of the subject under the set of conditions during a time different from the first period and the second period. The method further includes manipulating the first and second piezoelectric electrical signals using signal processing techniques and extracting from the manipulated first and second piezoelectric electrical signals a first cardiac electrical signal corresponding to the time of the second piezoelectric signal, where the first cardiac electrical signal related to at least one cardiac parameter.

In one aspect of the invention, the first piezoelectric electrical signal is obtained only once. The first period covers at least one full cycle of breathing activity and the second period covers at least one full cycle of cardiac activity. Further, the step of manipulating the first and second piezoelectric electrical signals includes: mapping a first part of the first piezoelectric signal corresponding to the at least one full cycle of the breathing activity in the first period to a second part of the first signal corresponding to the at least one full cycle of the cardiac activity in the second period; and determining a relationship between the first cardiac electrical signal and the second piezoelectric electrical signal using the mapping and the signal processing techniques.

In some embodiments of the invention, the mapping is performed using a linear one-to-one mapping. In other embodiments, different mapping techniques know in the art may be used.

In a related embodiment, the signal processing techniques described in the method include transforming the first and second piezoelectric signals into a frequency domain and generating a cardiac electrical signal extraction coefficient based on the first part and the second part of the first electrical piezoelectric signal.

In some embodiments, the method may further include storing the cardiac electrical signal extraction coefficient on a memory storage device along with the set of conditions used at the time of obtaining the first and second piezoelectric signals.

In a related embodiment, the step of extracting the first cardiac electrical signal includes one of: convolving the second piezoelectric signal obtained in the time domain with the inverse Fourier transform of the cardiac electrical signal extraction coefficient; and obtaining an inverse Fourier transform of the product of the cardiac electrical signal extraction coefficient with the second piezoelectric signal in the frequency domain.

In some embodiments of the invention, the step of obtaining the first piezoelectric electrical signal is performed when the subject is in good health condition. In other embodiments, the signal may be obtained when the subject is not in good health. The deficiency in the subject's health may be known or unknown.

In a related embodiment, the method further includes: determining a section of the first cardiac electrical signal corresponding to a single cardiac activity cycle and comparing the section with one cycle of the at least one cardiac activity cycle obtained in the second period; and assessing if the subject is healthy based on the comparison. Assessing if the subject is healthy comprises assessing the subject to have a positive condition or a negative condition based on the comparison.

In yet another related embodiment, the method further includes: determining a section of the second piezoelectric electrical signal corresponding to a single breathing activity cycle and comparing the section with one cycle of the at least one breathing activity cycle obtained in the first period; and assessing abnormalities in the subject's respiration or cardiac activity based on the comparison.

In some related embodiments of the invention, the at least one cardiac parameter is one of Aortic Pressure AP, Left Ventricle Pressure LVP, Left Atrial Pressure LAP, Left Ventricular Volume LV Vol, and heart sounds.

Some embodiments of the invention also include positioning the at least one piezoelectric sensor at any one of the subject's left upper body section, right upper body section or any part of the subject's lower body section, wherein the positioning of the sensors allows the subject to move freely without obstruction or limitation. The sensors weight and configuration also allow carry one with his or her daily routine without any disruption.

In a related embodiment, the subject is assessed to have the positive condition if the determined section of the first cardiac electrical signal is substantially similar to the one cycle of the at least one cardiac activity cycle obtained in the second period and wherein the subject is assessed to have the negative condition when the determined section of the first cardiac electrical signal is substantially dissimilar to the one cycle of the at least one cardiac activity cycle obtained in the second period.

In another related embodiment, the method further includes: notifying at least one of the subject and a third party of the positive or negative condition. The notification may be by any known means of communication. The notification may be provided in different forms and the message of the notification may vary and may be customized.

In some embodiments of the invention, the step of manipulating of the first and second piezoelectric electrical signals using signal processing techniques includes: wirelessly transmitting the first and second piezoelectric electrical signals using a transmitter; and receiving the transmitted first and second piezoelectric electrical signals using a receiver located at a location away from the transmitter. The step of extracting the first cardiac electrical signal is performed at the location of the receiver.

In a related embodiment, the method further includes: comparing each of the first and second piezoelectric electrical signals to a corresponding pre-determined threshold before transmitting it by the transmitter and amplifying any of the first and second piezoelectric electrical signal before transmitting them if any of the first and second piezoelectric electrical signals is determined to be below the corresponding pre-determined threshold. The method also includes comparing each of the first and second piezoelectric electrical signals to the corresponding pre-determined threshold after receiving it by the receiver and amplifying any of the first and second piezoelectric electrical signals after receiving them by the receiver if any of the first and second piezoelectric electrical signals is determined to be below the corresponding pre-determined threshold.

In some embodiments of the invention, the method further includes: storing in the memory storage device a plurality of first piezoelectric electrical signals obtained for the subject under a plurality of sets of conditions different from the set of conditions, wherein the conditions in the set of conditions and the plurality of sets of conditions relate to any combination of physical, physiological and environmental conditions under which the first piezoelectric signals are obtained.

In a related embodiment, the method further includes: comparing at least one full cycle in the first cardiac electrical signal to at least one full cycle in each of the plurality of first piezoelectric electrical signals in the second period; and assessing whether the subject has a cardiac activity abnormality based on the comparison.

In yet another related embodiment, the method further includes: comparing at least one full cycle in the second piezoelectric electrical signal to at least one full cycle in each of the plurality of first piezoelectric electrical signals in the first period; and assessing whether the subject has at least one of a respiratory or cardiac activity abnormality based on the comparison.

In some embodiments, the monitoring of the respiration activity is performed continuously and the step of obtaining the second piezoelectric signal comprises continuously obtaining additional piezoelectric electrical signals different from the first piezoelectric electrical signal. The additional piezoelectric electrical signals are obtained individually and sequentially after the first piezoelectric electrical signal. The additional piezoelectric electrical signals are based on additional mechanical movement of the body part related to the respiration activity of the subject. Also, additional respiration and cardiac electrical signals are extracted from the corresponding additional electrical signals. The method further includes: determining at least one cycle in each of the additional respiration and cardiac electric signals and comparing the determined at least one cycle with the at least one cycle of the respiration and cardiac activity, respectively, in the second period; and continuously assessing a health condition of the subject based on the comparison.

In a related embodiment, the method further comprises notifying at least one of the subject and a third party of the health condition of the subject. The notification may be by any known means of communication. The notification may be provided in different forms and the message of the notification may vary and may be customized.

BRIEF DESCRIPTION OF THE DRAWINGS

The accompanying drawings illustrate non-limiting example embodiments of the invention.

FIG. 8A to 8C show output voltage signals for the average cycle for excitation, respiration and hold breathing state, respectively, where the signals are generated from measurements obtained from the piezoelectric sensors in the system in FIG. 2.

DETAILED DESCRIPTION

Figure 1:
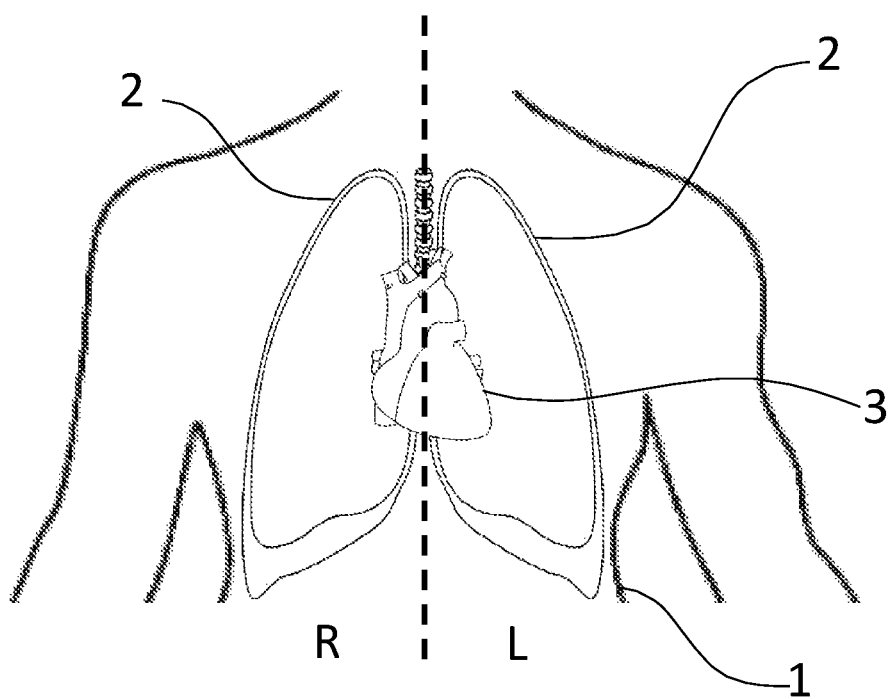
FIG. 1 shows a schematic illustration of a subject's upper body showing the position of the heart, lungs and thorax.

Throughout the following description specific details are set forth in order to provide a more thorough understanding to persons skilled in the art. However, well known elements may not have been shown or described in detail to avoid unnecessarily obscuring the disclosure. The following description of examples of the technology is not intended to be exhaustive or to limit the system to the precise forms of any example embodiment. Accordingly, the description and drawings are to be regarded in an illustrative, rather than a restrictive, sense.

The modelling of cardiac time domain impulsive response for any living organism that has a beating heart or organ, where such response contains the fine features as well as the pronounced chest functionality is not yet developed. This invention presents a method and apparatus which combines both piezoelectric and signal processing techniques to estimate such cardiac response for measuring heart activity without the need for using conventional means such as ECG machines. More specifically, the current disclosure describes a method and system for extracting cardiac cycle features from a respiration signal that is measured solely using piezoelectric sensors. A model is generated of the electrical signal corresponding to mechanical activity due to cardiac activity in relation to the mechanical activity due to respiration.

For the purpose of this disclosure, the respiration action defines the mechanical movement of the upper section of the subject's body due to the act of respiration. This movement is understood to include movements of the chest area and/or abdomen due to the mechanical movement of the lungs as the subject breaths as well as movement of the chest area due to the mechanical movement of the beating heart inside the body.

Piezoelectric based transducers technology could convert one form of energy into another. They have a range of uses, particularly as sensors. The piezoelectric effect has been used in thousands of sensing applications. These applications range from infrared sensors, stress gauges, and vibration detectors. The use of piezoelectric components can be quite advantageous, since the piezoelectric components would need fewer parts to fulfill the desired functionality.

Mechanical movement on the surface of a body of a living organism that has a beating heart and functional lungs is caused, at least in part, by mechanical movement of the internal organs such as the contractions and expansions of the heart muscles as well as the inflation and deflation of the lungs during breathing. The current disclosure may refer hereinafter to the activity of a heart or lungs in a human or a person or a subject; however, it is to be understood that the teachings in this disclosure cover activity of any moving organ in any living organism.

When piezoelectric material is attached to the person's body, such movement models a mechanical load and produces a relative induced strain on the piezoelectric material, which in turn causes the piezoelectric material to generate a corresponding conformal voltage signal. This voltage signal may be mapped with the heart's actions when the subject is in a state of holding breath. It may also be mapped with the respiration actions when the subject is in a state of breathing.

The resultant voltage signal may be used to extract and model the corresponding heart parameters using piezoelectric and signal processing theories. Furthermore, explicit expressions may be derived that relate the voltage output signal describing the heartbeat and other relative parameters based on the electromechanical coupling analogy. Different mapping techniques known in the art may be used. By way of non-limiting example, a linear one-to-one mapping may be used. Other mapping techniques may be used such as the ones disclosed in Al Taradeh et al., Non-invasive piezoelectric detection of heartbeat rate and blood pressure, Electronic Letters, Vol. 51, pages 452-454, 2015, the entirety of which is herein incorporated by reference.

The chest membrane of a subject exhibits the characteristics of bulky attenuator with certain time delay. FIG. 1 illustrates the left and right sides of a human chest 1, where the chest 1 is divided into a left side (L) and a right side (R). It incorporates both lungs 2 and the heart 3. The heart 3 along with lungs 2 physiological activities induce mechanical vibrations inside the chest wall. Such vibrations are correlated with the cardiac cycle features and the respiration rate, respectively. When a piezoelectric transducer is placed in position on the exterior surface of the chest; such induced vibrations will act as mechanical load on the piezoelectric transducer. The piezoelectric transducer correspondingly produces an electrical voltage signal that is conformally mapped with both respiration and cardiac activity. The lungs normally expand and contract up to 20 times per minute to supply oxygen to be distributed all over the body and expel carbon dioxide that has been created throughout the body. Meanwhile the heart muscle expands and contracts up to 100 times a minute to supply blood to the whole body.

Figure 2:
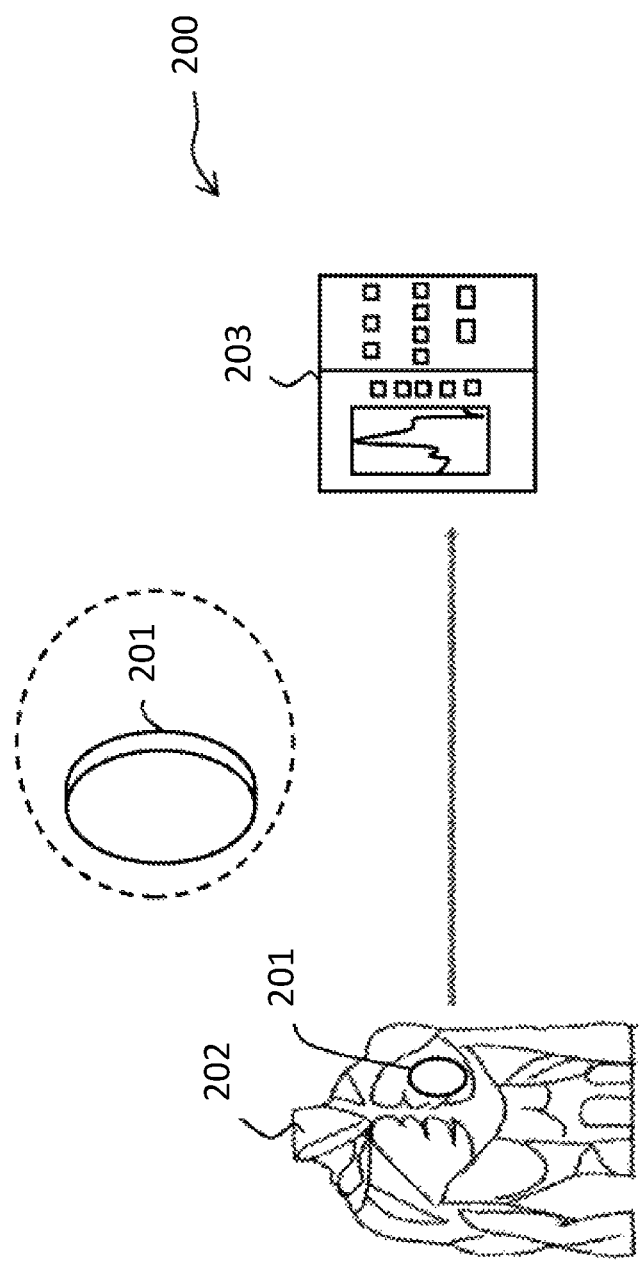
FIG. 2 shows a schematic representation of a cardiac and respiration monitory system according to an example embodiment.

FIG. 2 shows a schematic representation of a cardiac monitory system 200 in an exemplary embodiment of the invention. System 200 shows piezoelectric sensor 201 placed on the anterior chest surface of a person 202. The piezoelectric sensor 201 used in this embodiment is a sheet sensor (a DuraAct™ patch transducer); however other piezoelectric material known in the art may be used. Also, different configuration of the piezoelectric material known in the art may be used. As a non-limiting example, the piezoelectric sensor used may consist of a single sheet to capture various temporal signals, or it can be formed as an array of small piezoelectric sensors to capture the temporal and spatial cardiac signals over the chest to give an added spatial granularity on top of the localized temporal signal. In some embodiments described in this disclosure, the piezoelectric transducers have a size of 46 mm in length, 20 mm in width and 0.26 mm in thickness with composition of lead-zirconate-titanate (PZT). By way of non-limiting example, the table below provides select properties of some of the piezoelectric transducers that may be used. Other materials and parameters known in the art may be used.

| Dielectric constant | $\varepsilon^T_{11}$ | 4750 |
|---|---|---|
| Dielectric loss | tan δ | $25 \times 10^{-3}$ |
| Conductivity | σ | $<1 \times 10^{-12}$ 1/Ωm |
| Coercive field strength | $E_c$ | $570 \times 10^3$ V/m |
| Piezoelectric charge Constant | $d_{31}$ | 315 pm/V |
| | $d_{33}$ | 640 pm/V |

In FIG. 2, the output terminals of piezoelectric sensor 201 are connected to a digital oscilloscope 203. The connection may be wired or wireless. It is to be understood that all known forms of wired and wireless communication may be used to establish the connection between piezoelectric sensor 201 and oscilloscope 203. In some embodiments (not shown), the output terminals of the piezoelectric material may also be connected to a smart display through a microcontroller that can read the output voltage of the piezoelectric sensor.

In system 200, the periodic cardiac action of user 202 causes mechanical movement on the chest surface of user 202. Piezoelectric sensor 201, which is placed on the anterior chest surface of user 202, is then subjected to a mechanical load produced, at least, by the heart muscle's contractions and expansions when the subject is in a state of holding his breath. When the subject is in a state of breathing, the mechanical load produced may be contributed at least to the combination of the heart muscle's and lungs' contractions and expansions. The strain induced in piezoelectric sensor 201 generates a voltage. This energy conversion from the mechanical to the electrical is theoretically accounted for by a transformer with a turns ratio (not shown).

It can be argued that both cardiac and respiration features and their corresponding signals have the same excitation signal. This signal does exist but it cannot be measured directly. Excitation signal x(t) is embedded with chest wall functionality at the states of breathing and holding breath to yield the respiration signal $y_R(t)$ and heartbeat signal $y_H(t)$, respectively. Initially the excitation signal x(t) is of periodic nature with very small voltage amplitude. This assumption is supported by the causality principle.

The voltage signal generated by piezoelectric sensor 201 in FIG. 2 represents an instantaneous voltage output signal that may be displayed and recorded on oscilloscope 203 or a processor such as for example, a mobile device or a general processor using design code. In some embodiments (not shown), the output terminals of the piezoelectric material may be connected to one or more smart displays through one or more microcontrollers that can read the output voltage of the piezoelectric sensor.

Figure 4:
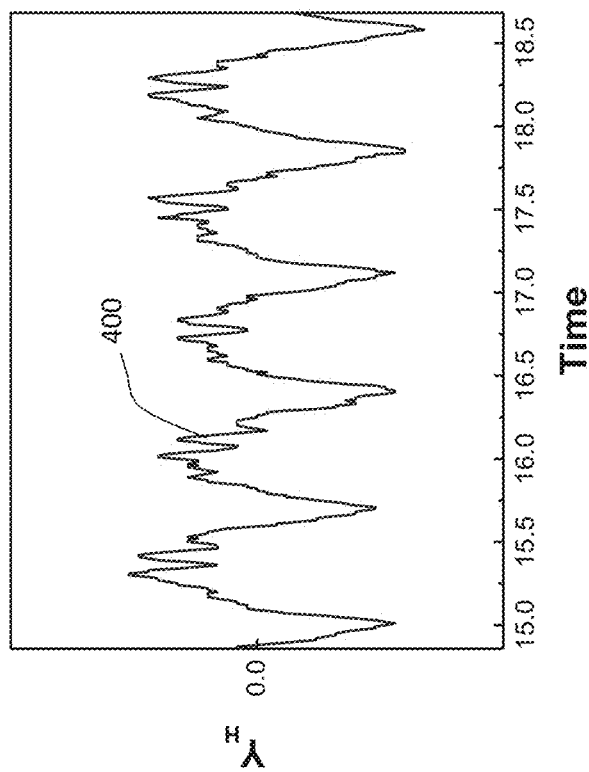
FIG. 4 shows an output voltage signal displayed on oscilloscope 3 in system 200 of FIG. 2, where the signal is obtained during a state of holding breath.
Figure 3:
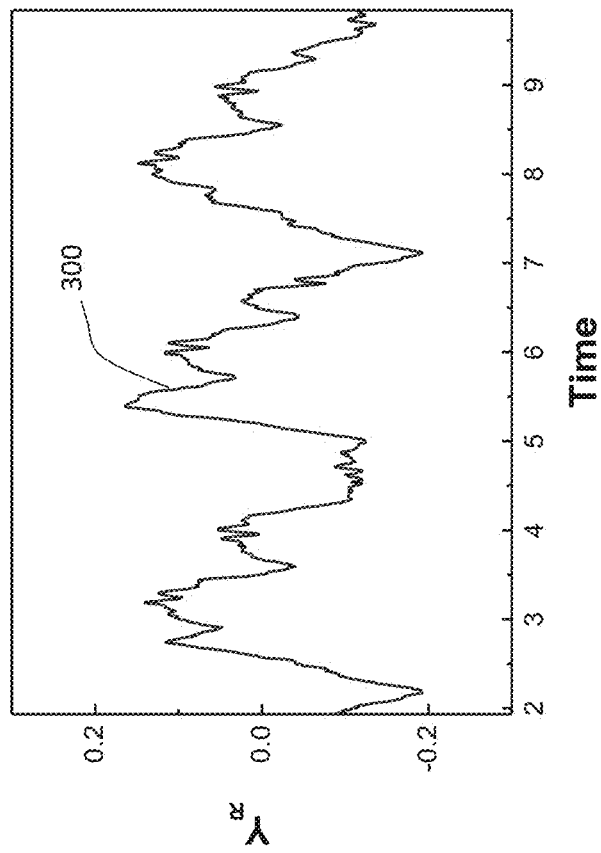
FIG. 3 shows an output voltage signal displayed on oscilloscope 3 in system 200 of FIG. 2, where the signal is obtained during a state of breathing.

FIG. 3 shows an output voltage signal 300 collating the respiration signal $y_R(t)$ along with the excitation signal x(t), where the signal is displayed on oscilloscope 203 in system 200 described above. FIG. 4 shows an output voltage signal 400 collating the hold breathing signal $y_H(t)$ along with the excitation signal x(t), where the signal is displayed on oscilloscope 203 in system 200 described above. As can be seen from FIGS. 3 and 4, the measured open-circuit signal output is of a periodic nature, where the subject is asked to breath normally for a period of time and then to hold his breath for a period of time under the same conditions as the breathing state.

When the subject is in the state of breathing, the corresponding output signal represents the excitation signal modulated by physiological activity of the lungs as well as the heart. The periodicity of this output signal is higher than the periodicity of the excitation. On the other hand, when the subject is at the state of holding breath, the corresponding output voltage from the piezoelectric transducer is modulated by physiological activity of the heart muscle and no activity is considered for the lungs at that state.

The period of a full cycle of normal breathing is longer than the period of a full cycle of a heart contracting and expanding causing the heartbeat. On average, a single full cycle of normal breathing by a subject may comprise three full cycles of a heartbeat. It is to be understood that this number may vary from one subject to another under the same conditions, or even for the same subject, due to different parameters such age, gender, weight or other physiological and physical known parameters of a subject. Also, the number may vary for the same subject if measurements are taken under different conditions such as the subject exercising or meditating for example. Under the same conditions for the same subject, the periodicity of the heartbeat is lower than the periodicity of a full breath cycle but nevertheless is still higher than the excitation signal.

Signals 300 and 400 are products of a multi-input, single output system, where the inputs may include, among others, cardiac parameters such as heartbeat and blood pressure for signal 400 and additional activity due to lung movement for the first section of signal 300. In some embodiments (not shown), the signal may also be a product of a multi-input, multi-output system. In order to extract the representation of cardiac parameters of interest from signals 300 and 400, piezoelectric theory and signal processing techniques are used.

As previously stated, induced stress in piezoelectric sensor 201 on the mechanical side is related to the output voltage produced in the sensors on the electrical side through the transformer. This induced stress is correlated with the real mechanical activity due to cardiac or respiration activity, which are conformally mapped with the corresponding output voltage signal. The equivalent turns ratio for the transformer is given by:

$$n = -d_{31} c_p / t_c \quad (1)$$

where $c_p$ is the elastic constant for the piezoelectric material, $t_c$ is the piezoelectric beam thickness and $d_{31}$ is the piezoelectric voltage constant.

The relation between the stress acting on the piezoelectric transducers, represented by p(t), and output voltage signal, V(t), is given by:

$$p(t) = n * V(t) \quad (2)$$

where n is the piezoelectric turns ratio representing the mechanical to electrical conversion process in the transducer.

Signal processing algorithms are used to map and extract the corresponding heartbeat signal from the respiration signal. By way of non-limiting example, the convolution process may be used to describe the relationship between the respiration signal $y_R(t)$, the heartbeat signal $y_H(t)$, the excitation signal x(t) and respiration and heartbeat corresponding impulse response functions $h_R(t)$ and $h_H(t)$, respectively, which are intrinsic to the system, as follows:

$$y_R(t) = x(t) * h_R(t) \quad (3)$$

$$y_H(t) = x(t) * h_H(t) \quad (4)$$

Where $y_R(t)$ is the measurable output voltage of the piezoelectric signal for respiration activity, $y_H(t)$ is the measurable output voltage of the piezoelectric signal for holding breath, where both $y_R(t)$ and $y_H(t)$ are forms of V(t), x(t) is the excitation signal and $h_R(t)$ and $h_H(t)$ are the impulse response of the chest wall functionality corresponding to respiration and holding breath, respectively, all in the time domain. The parameters $h_R(t)$ and $h_H(t)$ depend on several parameters including but not limited to at least chest wall thickness and human health conditions. It is to be understood that the same technique described herein may be used to extract signals specific to other physiological phenomena that may contribute to inducing mechanical stress on the piezoelectric material.

The objective of this disclosure is to identify, extract and quantify the heartbeat signal of a subject in real-time by considering the respiration signal of that subjection and with the use of only piezoelectric pressure sensors and signal processing techniques. As part of the initial setup, voltage measurements are collected from the piezoelectric sensors placed on the subject when the subject is asked to breath under specific conditions. Additionally, measurements are collected for the subject under the same conditions but with one difference, namely the subject is asked to hold his breath for a period of time. The conditions of interest may cover the physical and physiological state of the subject, environmental parameters and other conditions that may affect the respiratory and cardiac activity of the subject. This part of the initial setup may be repeated for different set of conditions.

The step of collecting voltage measurements from the piezoelectric sensors when the subject is holding his breath is performed only once as part of the initial setup and is not repeated afterward as long as the conditions, under which the measurements are collected is not changed. This step may be repeated however, when the conditions affecting respiration and cardiac activity are changed. This one time measurement of the voltage signal while the subject is holding his breath is used to establish a base that is used to construct the heartbeat signal for different times by extrapolating it from the respiration signal for these given times. The reason for having the subject hold his breath is to remove dependency of the piezoelectric generated electrical signal on mechanical movement related to the lungs and hence, the effect of respiratory cycle may be ignorable and excluded.

The one time measurement is to be understood to cover at least one full cycle of the cardiac activity but may also cover multiple cycles of the periodic cardiac activity, which may be averaged for more accuracy. For example, 10 or more cycles may be measured and averaged to allow for statistical accuracy. Given the periodic nature of the cardiac activity, a full cycle signal may best be identified as the signal falling between two peaks; alternatively, it can be generally identified between two points on a signal curve defining a full section which is periodically repeated in following sections. In some embodiments, system 200 may utilize an adaptive algorithm to detect the beginning of a cycle in a piezoelectric generated signal (not shown). A cardiac cycle is well known in the art and it refers to a complete heartbeat from its generation to the beginning of the next beat, and so includes the diastole, the systole, and the intervening pause.

It should be noted that the one time measurement is obtain for each subject the first time the system is used on such subject and also when the conditions under which the measurements are obtained change. Once these measurements are collected, the data obtained for that subject is stored by the system and used for future reference, so that in later use of the system, the subject is not required to hold his breath, as long as the subject's physiological and physical characteristics are substantially unchanged or as long as the conditions influencing the subject's cardiac and respiration activities are among the ones stored by the system. Such measurement may require updating if the subject experiences substantial physiological or physical changes, such as growth, aging, loss of weight or other physiological, physical or environmental changes known in the art that may affect the behaviour of the cardiac and respiration activity in the subject.

It is preferable that the one time initial measurement of the electrical signal generated by the piezoelectric sensors be carried out when the subject is in good heart health condition so that the measured signal may be stored and used to determine later if there is some discrepancy in the condition of the heart. Moreover, if the subject has heart problems, then the typical constructed signal from the mechanical model can be used as a reference, by adjusting it to the corresponding parameters based, at least on, age, weight and gender. Other physiological or physical parameters and/or characteristics may be taken into consideration as well. Therefore, in that case, the system may be able to discriminate between sick and normal heart by the indicators' status and also may be able to detect heart failure by prediction technique based on historical data that is stored by tracking the indicators. Indicators are to be understood as the set of parameters that are extracted from the one time initial measured signal.

For the respiration cycle, it is to be understood that the measurement is to cover at least one full cycle of the respiration activity but may also cover multiple cycles of the respiration activity, which may be averaged for more accuracy. For example, 10 or more cycles may be measured and averaged to allow for statistical accuracy. Traditionally, a full cycle of respiration is considered as a cycle that includes a full inhalation action followed by a full exhalation action. However, this definition is limiting. Given the periodic nature of the respiration activity under the same conditions and without external or internal factors that may affect the breathing of the subject, a full cycle signal may best be identified as the electrical signal falling between two peaks. Alternatively, it can be generally identified between two points on a signal curve defining a full section which is periodically repeated in following sections. In some embodiments, system 200 may utilize an adaptive algorithm to detect the beginning of a cycle in a piezoelectric generated signal (not shown).

The respiration initial signal may be stored and then used for comparison with the respiration signal at a later time for diagnosis of any irregularities in respiration. Such diagnosis may allow for detection of abnormalities in lungs activity by examining the respiration signal and comparing it to the reference respiration initial signal.

It is preferable that in the initial setup, the period selected for measuring the respiration signal and the one for measuring the signal while the subject is holding his breath is equal or substantially equal. However, in some embodiments, this may not be required and averaged cycles for both respiration and cardiac activity may be used.

Referring back to equations (3) and (4), once $y_R(t)$ and $y_H(t)$ are obtain for the initial use and under the same conditions, a Fourier transform may be applied to the equations to result in:

$$Y_R(f) = X(f) H_R(f) \quad (5)$$

$$Y_H(f) = X(f) H_H(f) \quad (6)$$

Where equations (5) and (6) are the frequency representation of equations (3) and (4), respectively and $Y_R(f)$, $Y_H(f)$, $X(f)$, $H_R(f)$ and $H_H(f)$ are corresponding Fourier transformers of $y_R(t)$, $y_H(t)$, $x(t)$, $h_R(t)$ and $h_H(t)$, respectively. The chest-side impulse response for respiration and holding breath signals in the frequency domain may be obtained by manipulation equations (5) and (6) to obtain the following:

$$H_R(f) = \frac{Y_R(f)}{X(f)} \quad (7)$$

$$H_H(f) = \frac{Y_H(f)}{X(f)} \quad (8)$$

Equations (5), (7) and (8) may be manipulated in order to express the respiration signal in terms of the holding breath signal in the frequency domain as follows:

$$Y_H(f) = \frac{Y_R(f)}{H_R(f)} H_H(f) \quad (9)$$

Rearranging equation (9) and taking the inverse Fourier transform yields:

$$y_H(t) = F^{-1}\left[\frac{H_H(f)}{H_R(f)} Y_R(f)\right] \quad (10)$$

Equation (10) expresses the electrical signal of the cardiac activity of the subject at any point in time in terms of electrical respiration signal measure by the piezoelectric sensors for the same point in time. For simplicity, a term $Q(f)$ may be introduced to substitute for the ratio of the impulse response functions $H_H(f)$ to $H_R(f)$ (i.e. $Q(f)=H_H(f)/H_R(f)$) as follows:

$$y_H(t) = F^{-1}[Q(f) Y_R(f)] \quad (11)$$

Referring to equations (5) and (6), $Q(f)$ may also be expressed as follows:

$$Q(f) = \frac{Y_H(f)}{Y_R(f)} \quad (12)$$

It is assumed that the impulse responses of the chest functionality $h_R(t)$ and $h_H(t)$ and their corresponding frequency domain values, $H_R(f)$ and $H_H(f)$, maintain their value in the time and frequency domain, respectively, as long as the conditions, under which the initial measurements are obtained, are unchanged. Therefore, using equation (12), inserting into that equation the measurements collected from the initial setup for the respiration period and the holding breath period, where both periods may be the same or different, the ratio $Q(f)$ may be expressed as follows:

$$Q_o(f) = \frac{Y_{o_H}(f)}{Y_{o_R}(f)} \quad (13)$$

where $Y_{o_H}(f)$ and $Y_{o_R}(f)$ represent the initial measurements collected for the holding breath signal and respiration signal, respectively, for the same period and where $Q_o(f)$ is considered a constant as long as the conditions, under which the first initial measurements are collected, are unchanged. Therefore, substituting equation (13) into (11) yields:

$$y_H(t) = F^{-1}[Q_o(f) Y_R(f)] \quad (14)$$

The heartbeat signal may also be constructed directly in the time domain by using equation (12) and the Fourier transform on $Q_o(f)$ as follows:

$$y_H(t) = Q_o(t) * y_R(t) \quad (15)$$

The method described in equation (15) provides for a technique for constructing the cardiac activity signal for a subject at any point in time by only measuring the respiration signal of the subject at that point in time using piezoelectric sensors placed on the subject's body. The method also requires an initial setup in which the piezoelectric sensors are used to collect at least one initial set of electrical signals for the subject when the subject is in a breathing state as well as in a hold breathing state for the same period of time and under the same conditions. Such method may be applied in real time and no other measurements or traditional equipment are required to determine the cardiac activity signal of the individual at any given point in time.

It should be noted that when the initial respiration and holding breath signal measurements are obtained for multiple cycles, averaging of the signal may be done before or after transforming the function into the frequency domain. Also, the Fourier transform may be applied at the end of the cycle or any point through the cycle. Additionally, given that the respiration period is longer than the heartbeat period, it is possible in some embodiment to average the respiration cycles of the initial measured respiration signal to achieve one respiration cycle. It is also possible to do the same to achieve an averaged single heartbeat cycle from the measured signal in the holding breath state. However, in such case, care should be taken to determine the number of heartbeat cycles for one respiration cycle under the same conditions and to factor this information in calculating $Q_o(f)$ in equation (14).

Figure 5:
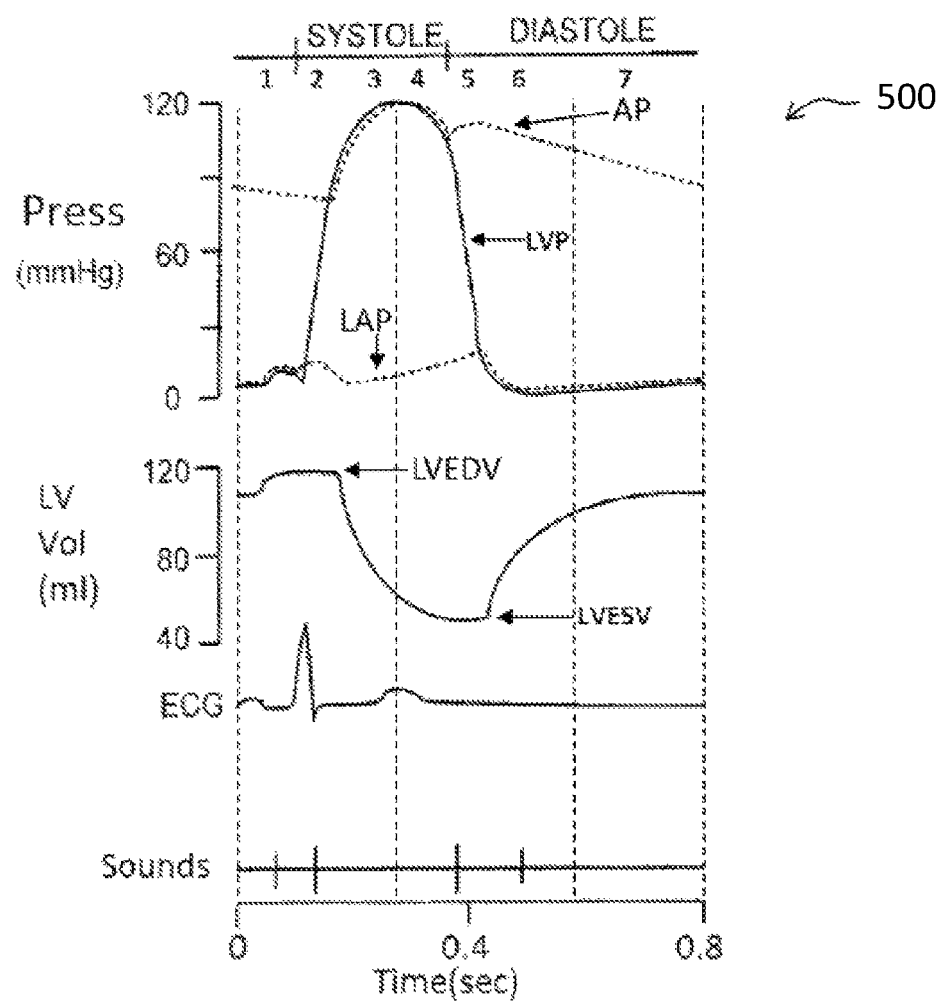
FIG. 5 shows a diagram which shows other cardiac cycle parameters including but not limited to Aortic Pressure (AP), Left Ventricle Pressure (LVP), Left Atrial Pressure (LAP), Left Ventricular Volume (LV Vol), and heart sounds, that could be found with the same manner during a single cycle of cardiac contraction and relation.

It is to be understood that the technique presented above may be applied to extract other cardiac activity parameter different than the heartbeat. FIG. 5 shows a diagram 500 which shows other cardiac cycle parameters including but not limited to Aortic Pressure (AP), Left Ventricle Pressure (LVP), Left Atrial Pressure (LAP), Left Ventricular Volume (LV Vol), which shows the left ventricular end diastolic volume (LVEDV) and the left ventricular end systolic volume (LVESV), and heart sounds, that could be found with the same manner during a single cycle of cardiac contraction and relaxation.

Figure 6:
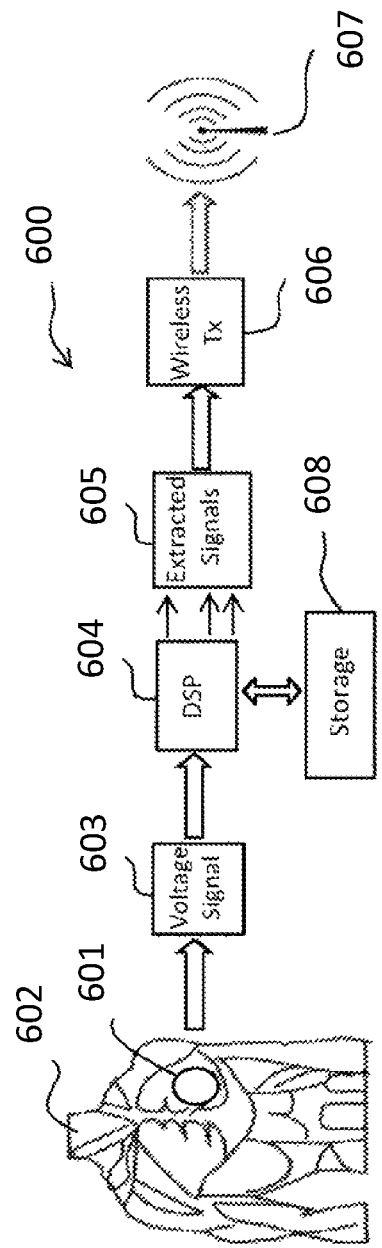
FIG. 6 shows a schematic representation of a cardiac monitory system 600 according to another embodiment of the invention.

In some embodiments such as system 600 provided in FIG. 6, system 600 may include a processor and a memory storage device (604 and 608, respectively in FIG. 6). The processor and memory device may be provided in a same device or in separate devices. FIG. 6 shows the processor and the storage device separate. The processor may apply an adaptive algorithm to detect the beginning of a cycle in the piezoelectric generated electrical signal for the initial respiration and holding breath signals and to average the cycles once full cycles are identified. The processor may then determine the ratio between the initial measured respiration signal and holding breath signal using the Fourier and inverse Fourier transform operators to determine $Q_o(f)$. Different $Q_o(f)$ may be determined for different set of conditions under which the initial measurements were taken. The different $Q_o(f)$ along with their corresponding conditions may be stored on the memory storage device for later reference and access by the processor.

When the system is used by the same subject at a later time, the respiration measurements of the subject are collected for that time using the piezoelectric pressure sensors placed on the subject's body. The conditions under which the new respiration measurements are collected are identified by the processor and the processor then accesses $Q_o(f)$ from the memory storage device corresponding to such conditions. Based on $Q_o(f)$ and the newly measured respiration signal, the processor constructs an electrical signal representative of a specific cardiac parameter such as the heartbeat, which corresponds to the newly measured respiration signal.

The processor may then access the initial holding breath signal previously stored for the same subject under the same conditions and compare it to the new generated representative signal using auto-correlative correlation. If the result of the correlation is found to be high, the processor may then yield a notification indicative of a good result or a bad result to the user if the correlation is found to be high or low, respectively. In some embodiments (not shown), pre-determined values are set as threshold on which assessment values are compared and based on the comparison, the evaluation of a good or a bad correlation is provided by the processor. Such pre-determined values may vary from one subject to another and may vary for the same subject based on gender, age, weight and other philological, physical and/or environmental parameters and characteristics known in the art.

The memory storage device may also include at least one pull-up library of initial holding breath and breathing measurements and their corresponding conditions for signals representing known cardiac and/or respiratory defects for different individuals. Such signals may include marker regions and may be classified in the pull-up library by age, gender, weight, or other physiological, physical and/or environmental parameters and characteristics. When the system is used by the same subject described above, in addition to the process described above, the processor may also access some of the stored signals in the pull-up library, based on conditions initially provided about the subject, and performs a cross correlation comparison between each one of the signals selected from the pull-up library and the piezoelectric representative signal generated for a specific cardiac parameter for the subject. If the result of the correlation is found to be higher than a pre-determined value around the region representing the cardiac defect, the processor may then yield a notification indicative of a possible diagnosis of the cardiac disease. If the result of the correlation is found to be lower than a pre-determined value around the region representing the cardiac defect, the processor may then yield a notification indicative of a normal reading or a notification indicative of the tested disease and the lack of presence of indicators of concern relating to that disease. Different notification, alerting and warning techniques known in the art may be used to convey the output of the system.

In the embodiments described above, the system may also include a wired or wireless transmitter (not shown). The processor may communicate, using the transmitter, a message or a notification to the subject being examined and/or to a third party based on the results obtained. By way of non-limiting example, the message may provide that the subject is in need of a check-up by a physician. The message may include the signal generated in a format familiar to the physician so that it may be used directly for making a diagnosis. If the subject is in distress, the message may be communicated to an emergency unit to provide the subject with some emergency care. The message may also include information about the subject as well as the location of such individual.

FIG. 6 shows a schematic representation of a cardiac monitory system 600 according to another embodiment of the invention. In system 600, electrical signal 603 in the respiration state is generated by piezoelectric sensors 601 located on or near the chest of user 602. Signal 603 is then manipulated using digital signal processing and piezoelectric theory, shown to occur in processor 604 in FIG. 6, as described above, to extract signals relating to particular cardiac parameters, which is shown as 605 in FIG. 6. System 600 further provides a transmitter 606, which is used to transmit the extracted signals wirelessly in accordance with any known wireless transmission techniques known in the art. The transmitted signal is then received by a receiver, shown in FIG. 6 as 607. The receiver may be in proximity to the subject and the processing of the signal once received may also be done in proximity of the subject.

In some embodiments, the signal processing may be performed away from the subject. In such embodiments (not shown), piezoelectric sensors may be attached to the subject and a transmitter may be either attached to the subject or may be carried by the subject. The transmitter may be located at a distance away from the sensor to reduce noise and/or interference.

In some embodiments, more than one piezoelectric pressure sensor may be used for signal calibration and also for obtaining signals from different positions on the subject's body. FIG. 7A shows two identical piezoelectric transducers, where the first sensor PZE1 is placed on the right side of the subject's chest and the other sensor PZE 2 is placed on the left side. The setup provided in the system described in FIG. 2 or 6 may be used for collecting the voltage output signal from the corresponding side as well as viewing and manipulating the data obtained from PZE 1 and PZE2.

Figure 7B:
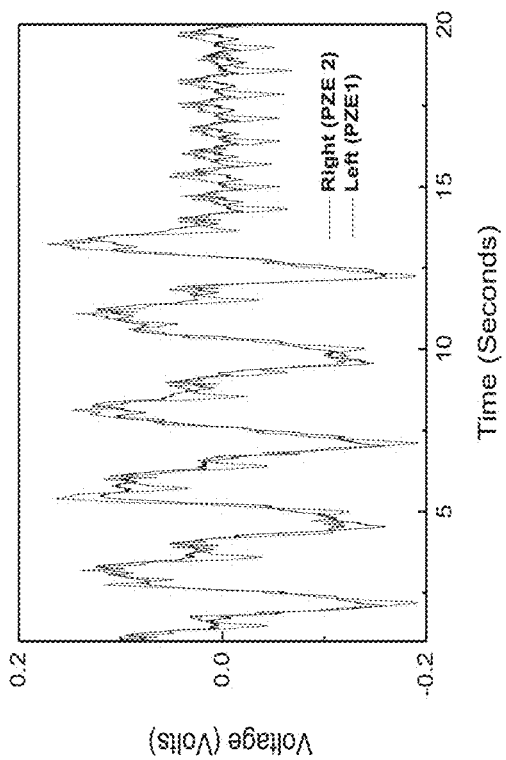
FIG. 7B shows an output voltage signal generated from the measurements obtained from the piezoelectric sensors in FIG. 7A for a period of 20 seconds, where a section of this period represents the signal measured while the subject is breathing and the other section of this period represents the measured signal when the subject is in a state of holding breath.
Figure 7A:
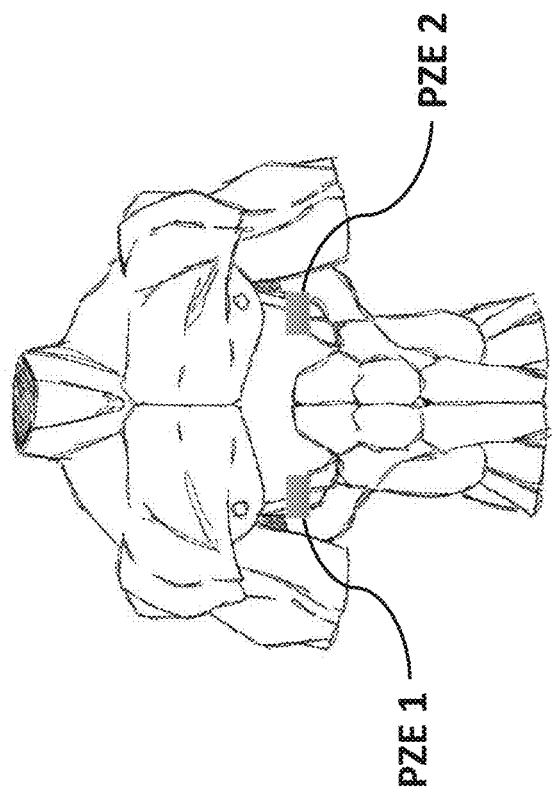
FIG. 7A shows a schematic representation of a subject's torso, where two piezoelectric sensors are placed on the subject's torso and are used to measure output signals from the left and right side of the chest using the system described in FIG. 2.

FIG. 7B shows the output voltage signal measured by the system when the piezoelectric sensors are positions as per the setup described in FIG. 7A. In this embodiment, the subject was asked to breath normally under no physical, physiological or environmental stress for 15 seconds. The subject was then asked to hold his breath for the next 5 seconds under the same conditions. FIG. 7C shows the voltage output signal of FIG. 7B but only for the period covering the hold breathing signal. FIG. 7B clearly shows the difference in periodicity of the signals for the respiration and holding breath states.

Also, in FIGS. 7B and 7C, it is observed that the signals collected from the right and left side piezoelectric transducers do not generate identical signals. This may be contributed to the positioning of the sensors relative to the source of mechanical vibrations caused by heart and lungs activity as well as relative to one another. In some cases for example, the difference may be described as a phase shift (or a change in time period). In other cases, the difference may be reflected by one signal being stronger than the other (or a change in amplitude). In the embodiment shown in FIG. 7B, the difference between the signals is uniform; however, this may vary in other embodiments depending on the position of the sensors relative to the source of the vibration as well as to one another.

Figure 7D:
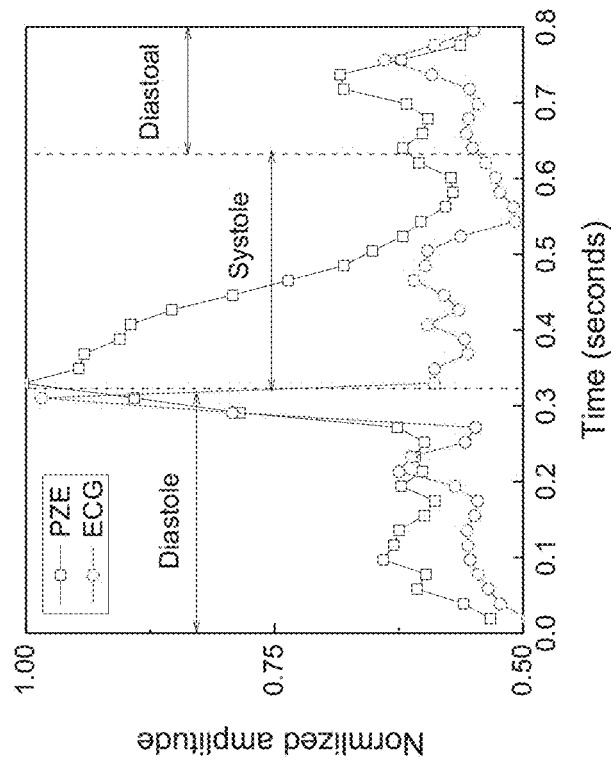
FIG. 7D shows a comparison between a single cycle of an electrical piezoelectric signal measured using the system in FIG. 2 and a normalized ECG measured signal showing the systolic and diastolic ranges.
Figure 7C:
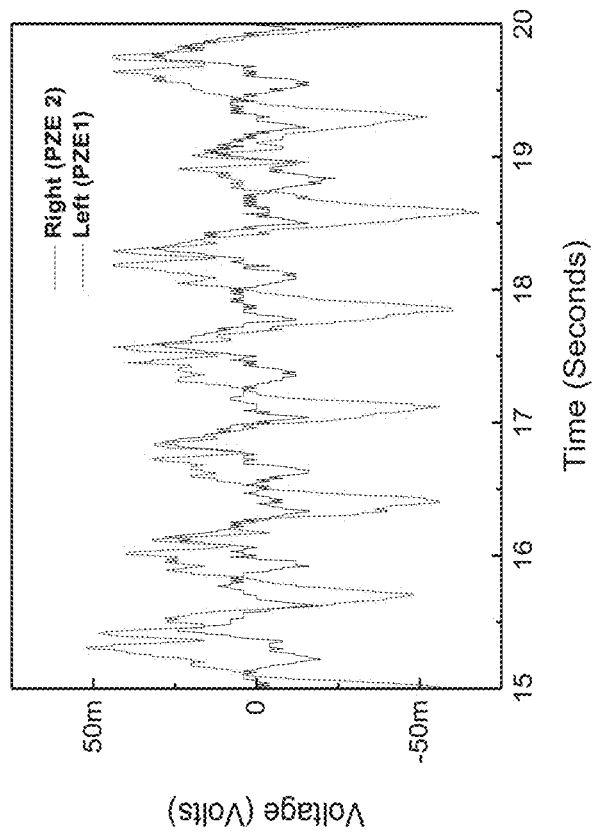
FIG. 7C shows the output voltage signal for the last five seconds of the signal presented in FIG. 7B.

For verification purposes, a normalized ECG measured signal is compared with the piezoelectric output signal for one cycle from FIG. 7C and the comparison is presented in FIG. 7D. By superimposing the two signals, FIG. 7D shows the periodic nature of both ECG and piezoelectric signals with time interval of 0.8 second for both signals.

In the description above, the ideal positioning of the piezoelectric sensors is in areas on the chest close to the organ producing the cardiac mechanical movement, i.e. the heart. This is because the chest is understood to act as a bulky chest membrane that dampens the mechanical movement. Therefore, the closer the piezoelectric sensors are placed to the source of the mechanical movement, the stronger the mechanical movement detected and therefore, the stronger the electrical signal generated. However, given that the measured signal is also due to respiration, placement of the sensors may be on other parts of the chest. Further, with use of amplifiers and signal-to-noise enhancement techniques known in the art, it may be possible to position the piezoelectric sensors on a part of the subject's body different than the chest area and still be able to achieve a compatible and compact contactless probing system with the ability to model the impulsive response incorporating the cardiac cycle parameters based on measured respiration signals.

Figure 8C:
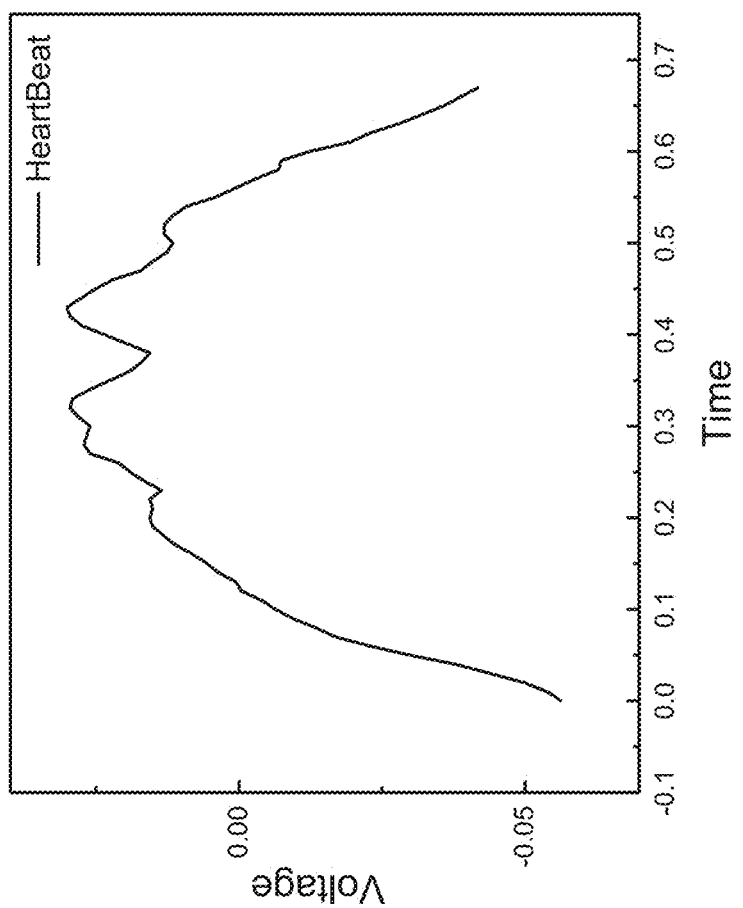
Figure 8E:
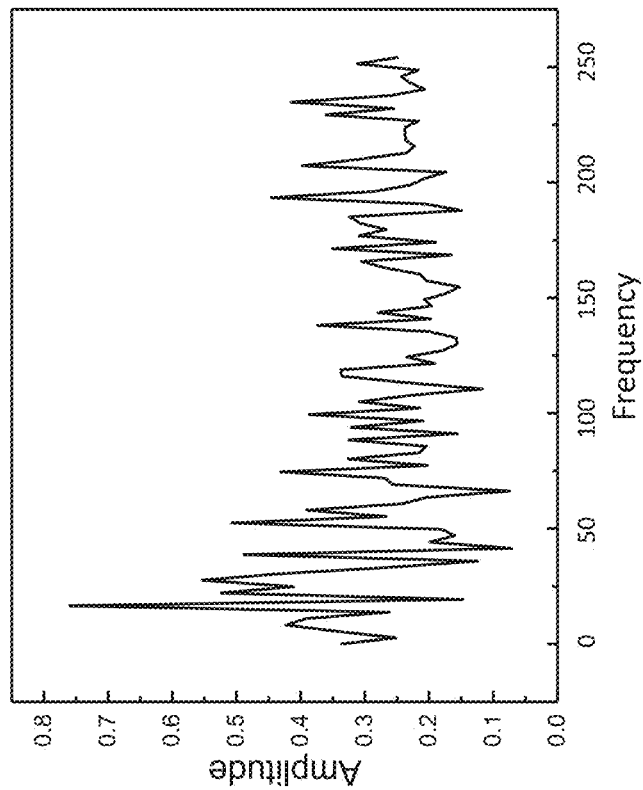
FIG. 8E shows the ratio in the frequency domain of the holding breath state impulse response of the chest wall functionality over the respiration impulse response of the chest wall functionality.
Figure 8D:
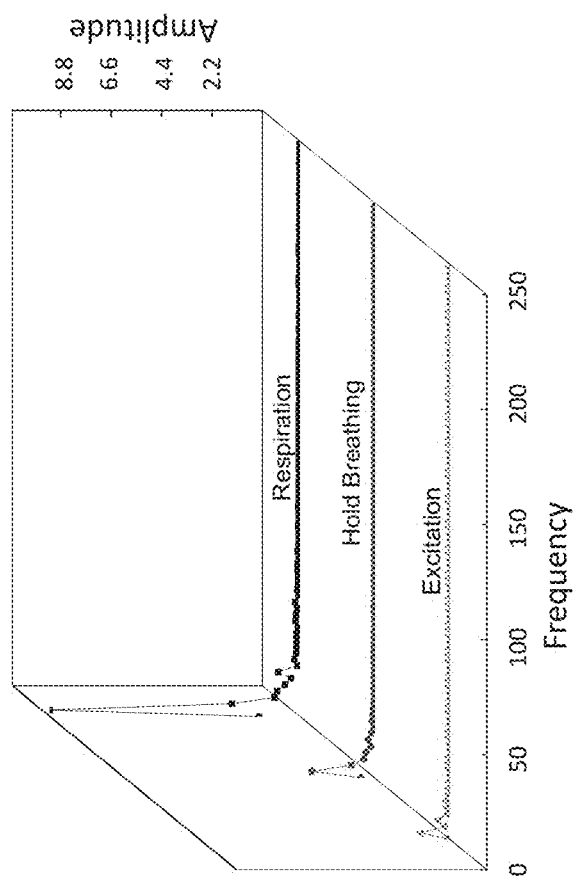
FIG. 8D shows corresponding frequency domain signals for the excitation, respiration and hold breathing state signals shown in FIGS. 8A to 8C, respectively.

FIGS. 8A to 8E represent a sample embodiment of the invention described above. In This example, the voltage output signal measured from the piezoelectric sensors is interpolated to the smallest periodicity. As noted above, this invention allows for extracting the cardiac activity signal from the respiration signal based on at least one full measured cycle of the respiration signal. Measuring more than one cycle allows for averaging, which allows for increasing accuracy. In the example presented in FIGS. 8A to 8E, the time domain average cycle is first calculated for each signal. All signals were individually detached into cycles for averaging. The average cycle for excitation, respiration and holding breath are shown in FIGS. 8A to 8C, respectively. FIG. 8D shows the corresponding frequency domain signals for the excitation, respiration and holding breath averaged signals, which have been computed using Fourier transform. In FIG. 8D, the magnitudes of the signals were plotted against the frequency. FIG. 8E shows the magnitude of the frequency domain of the impulse responses of the chest wall functionality at holding breath $H_H(f)$ and respiration $H_R(f)$. These responses have been computed using equations (7) and (8), respectively. Furthermore; the $Q_o(f)$ function was determined by taking the ratio of $H_H(f)$ over $H_R(f)$.

Figures 9A, 9B:
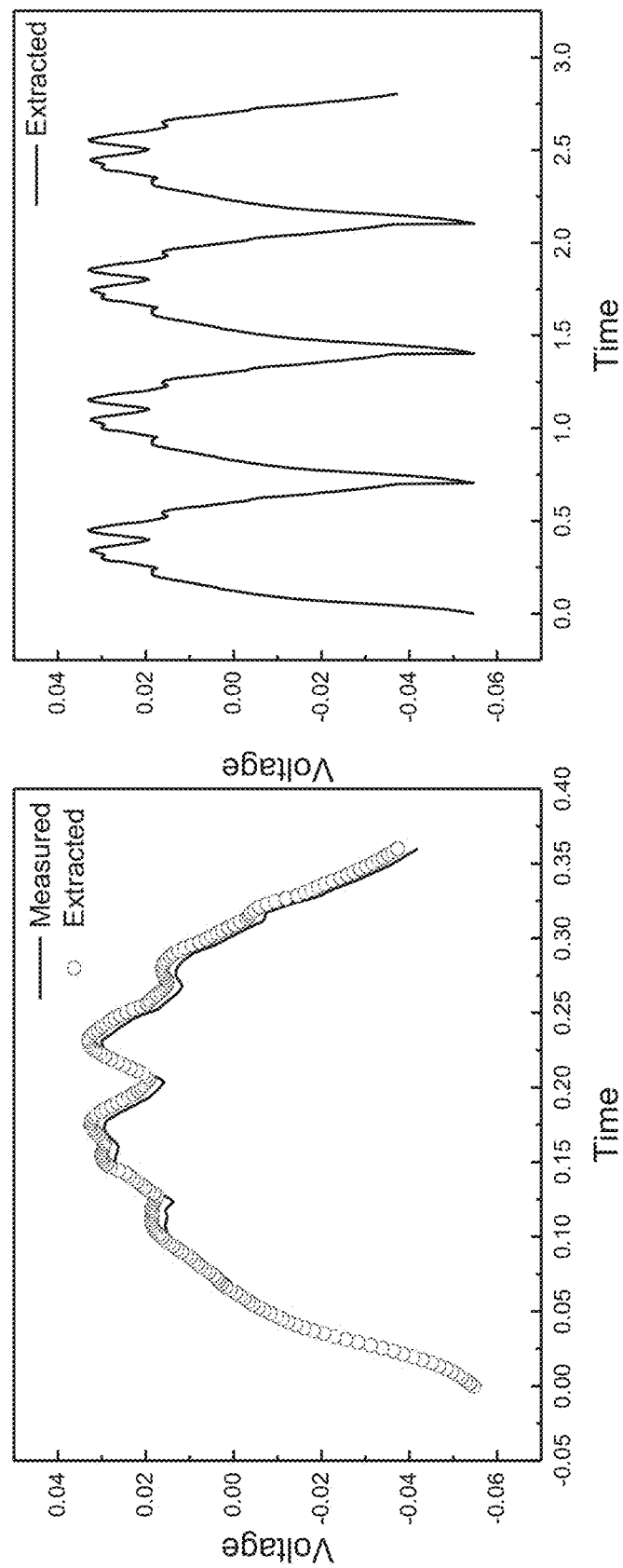
FIG. 9A shows the cycles of the heartbeat electrical signal reconstructed from the magnitude signal in the frequency domain via Fourier transfer, where the signal is superimposed on the initial measured signal at the hold breathing state using the system shown in FIG. 2.
FIG. 9B shows the cycles of a heartbeat electrical signal reconstructed for a hold breathing state, where the signal corresponds to a single respiration cycle.

Using equation (14), the average cycle of the heartbeat signal is constructed from the magnitude of the frequency domain via inverse Fourier transform. FIG. 9A shows the constructed heartbeat signal from the respiration signal according to the current disclosure. On the same figure, the initial measured cycles for holding breath are superimposed on the constructed signal. FIG. 9A, shows that the two superimposed signals are substantially similar. This reflects that the constructed heartbeat signal is highly accurate when compared to the initial measured signal of the holding breath signal that represents the initial measurement of the heartbeat signal under the same conditions.

FIG. 9B shows a constructed holding breath electrical signal corresponding to a single respiration cycle. According to the example provided, a single respiration cycles occurs in a time period that is sufficient to allow four full cycles of heartbeat signals. This number may vary from one individual to another and may also vary for the same individual subject to varying physiological, physical and/or environmental conditions.

Figure 10B:
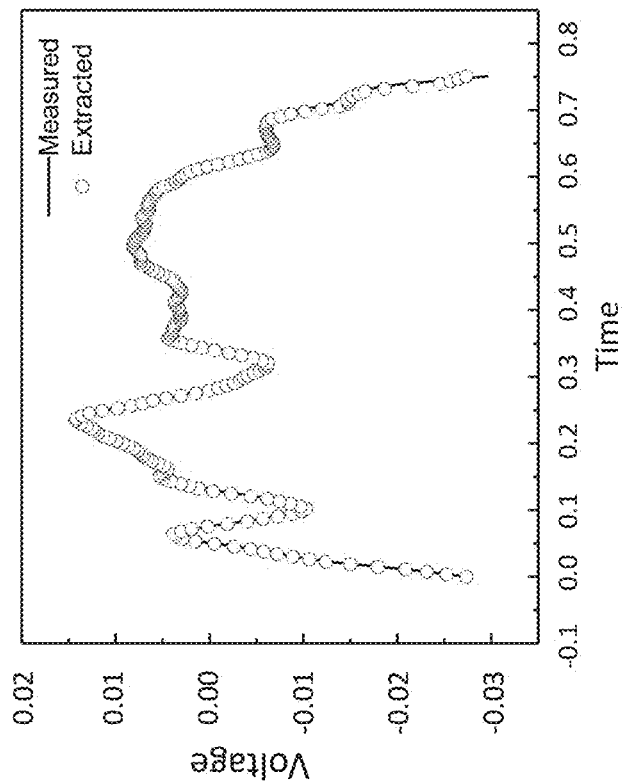
FIG. 10B shows the extracted signal for holding breath state from the signal shown in FIG. 10A superimposed on the measured signal for the holding breath state for the same subject.
Figure 10A:
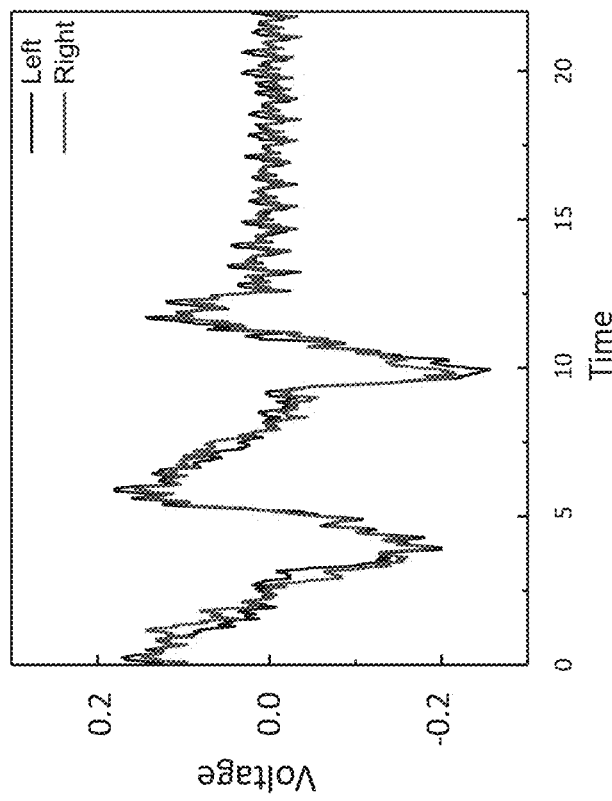
FIG. 10A shows output piezoelectric voltage signals for excitation, respiration and holding breath state measured from left and right sides of a different subject using the system described in FIG. 7A.

FIG. 10A shows the respiration excitation signal along with the holding breath signal collected from the right and left side of the chest as presented in FIG. 7A for a subject different from the subject of FIG. 9A. The constructed heartbeat signal is generated using the technique described in this disclosure and is shown in FIG. 10B. This is superimposed on the signal measured for that person during the initial setup stage while the subject is in a holding breath state under the same conditions. A comparison between the two signals in FIG. 10B show a high degree of similarity, which imply a high degree of accuracy of the constructed heartbeat signal based on the respiration signal.

Furthermore, a comparison between FIG. 10B and FIG. 9A show that the heartbeat signal for different individuals may be different from one another but that the constructed heartbeat signals are accurate and uniform when calculated for the same individual. Additionally, the comparison also shows the ability of the system and technique to be used to construct heartbeat signals utilizing piezoelectric sensors placed away from the heart position. This in turn provides a distinct advantage for using this system for patients that are not allowed to use electrical devices near their heart. In such circumstance, the system and technique disclosed allows the patient to place the piezoelectric transducers away from the heart position and for example to the right side of the chest instead of the left side. The system and method also allow for the development of new sensor generation to detect and identify respiration and heart abnormalities passively, non-invasively, without the need to restrict or limit the subject's movement and also without the need for the subject to carry with him equipment that may disrupt his daily routine.

Figures 11A, 11B:
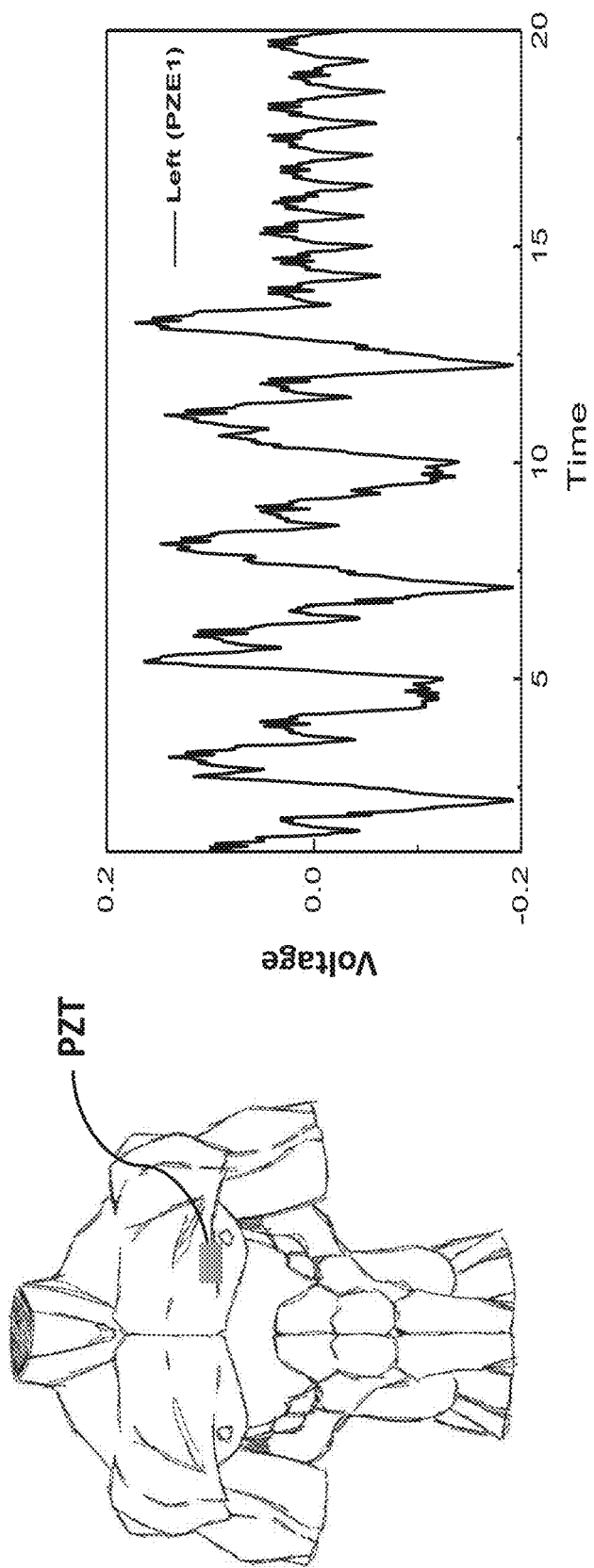
FIG. 11A shows a schematic representation of a subject's torso, where only one piezoelectric sensor is placed on the subject's torso on the position corresponding to the $4^{th}$ rib of the thorax at the left front side of the chest, where the sensor is used to measure the output signal using the system described in FIG. 2.
FIG. 11B shows an output voltage signal generated from the measurements obtained from the piezoelectric sensor in FIG. 11A for a period of 20 seconds, where a section of this period represents the signal measured while the subject is breathing and the other section of this period represents the measured signal when the subject is in a state of holding breath.
Figure 12A:
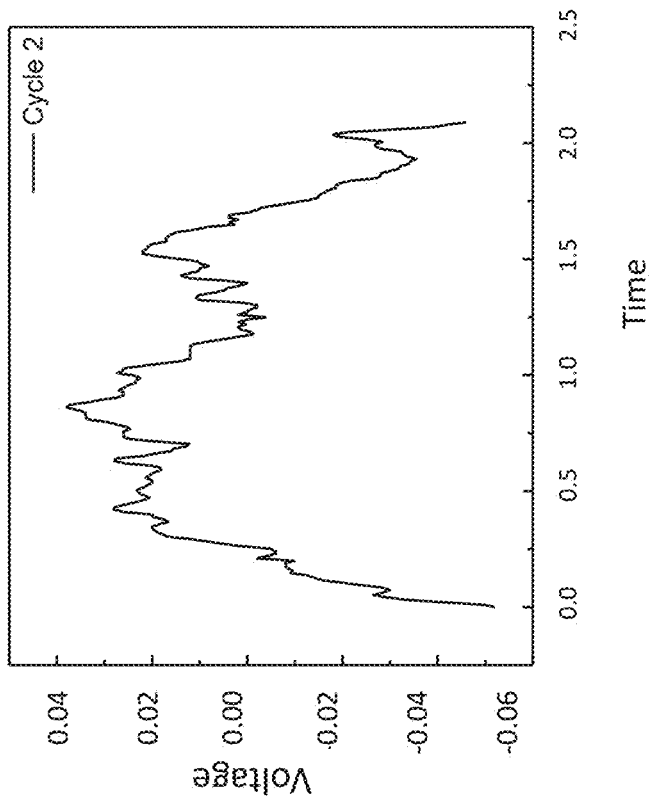
FIG. 12A to 12D show the electrical signals corresponding to the first four full respiration cycles shown in FIG. 11B, respectively.
Figure 12B:
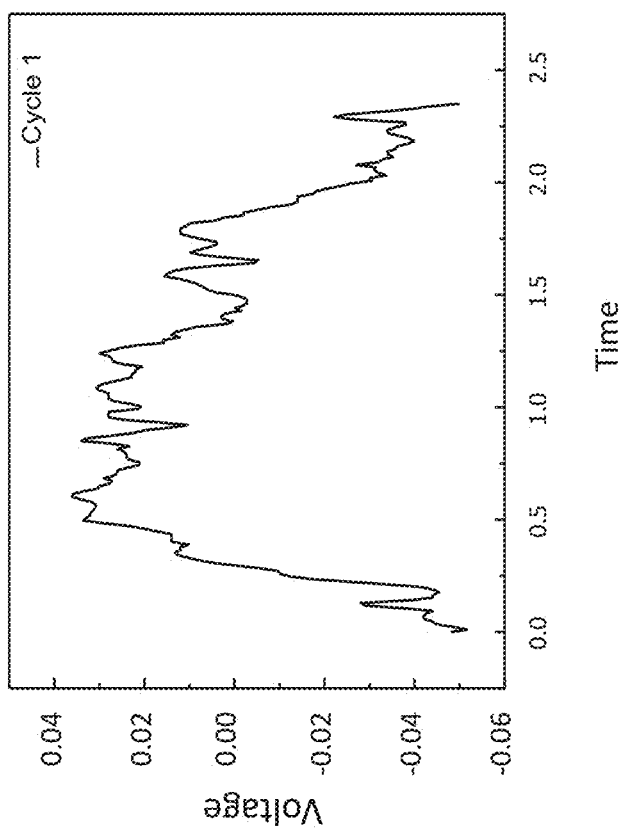
Figure 12C:
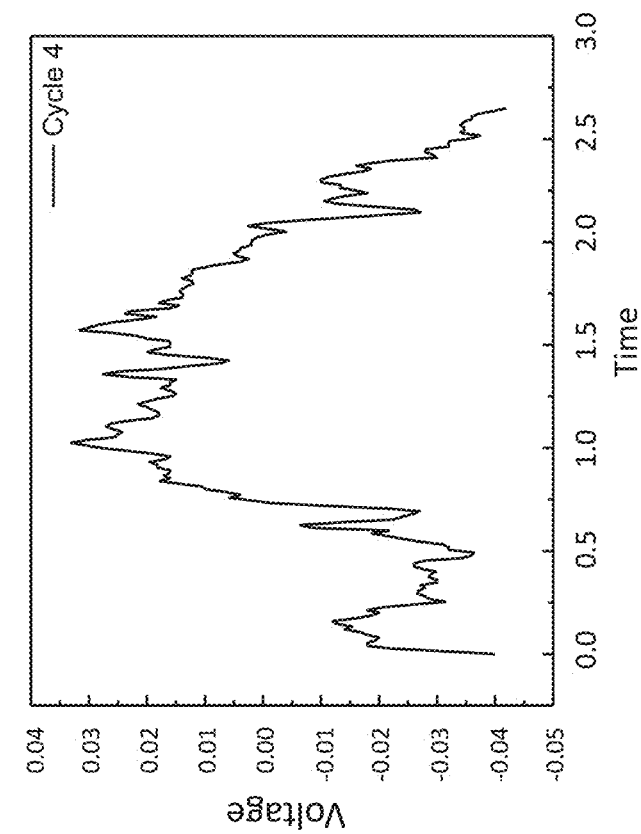
Figure 12D:
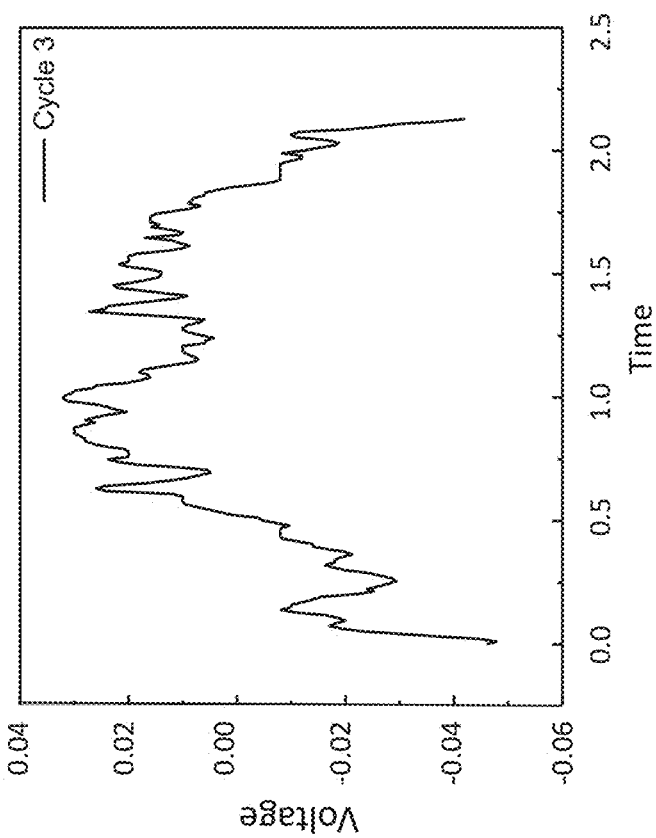
Figure 12F:
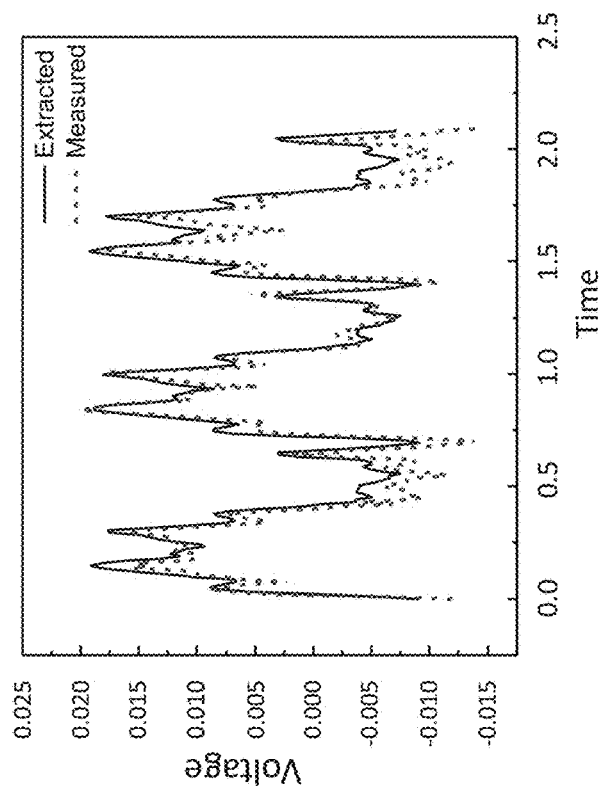
FIG. 12E to 12H show the extracted heartbeat signal corresponding to the respiration cycles shown in FIGS. 12A to 12D, respectively, in accordance with the method described in the current disclosure and where the extracted heartbeat signal is superimposed on the initial measured piezoelectric signal obtained when the subject is in a hold breath state.
Figure 12E:
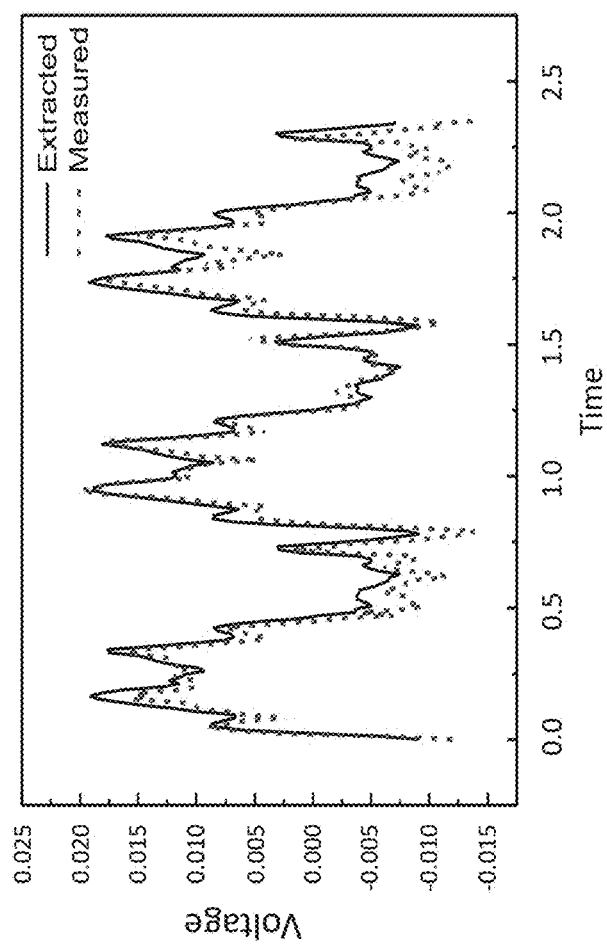
Figure 12H:
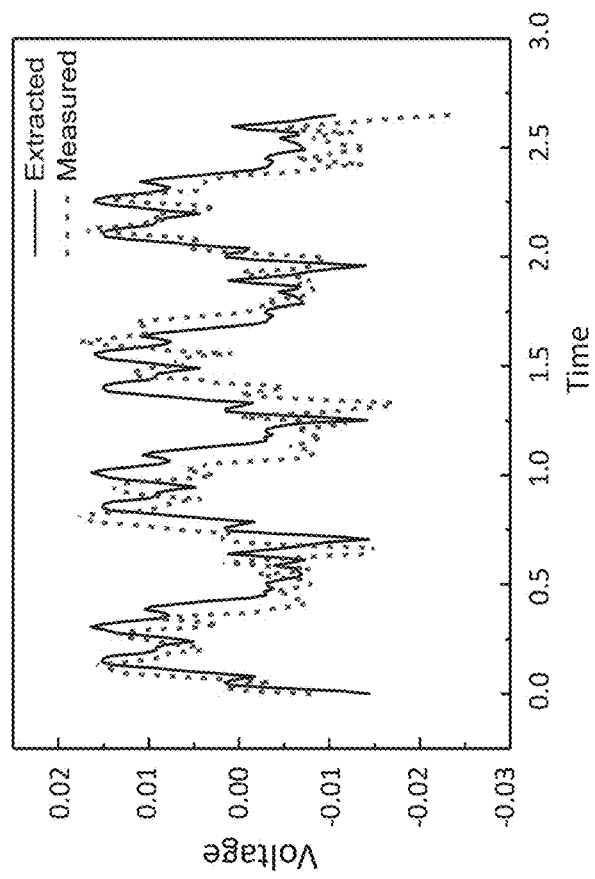
Figure 12G:
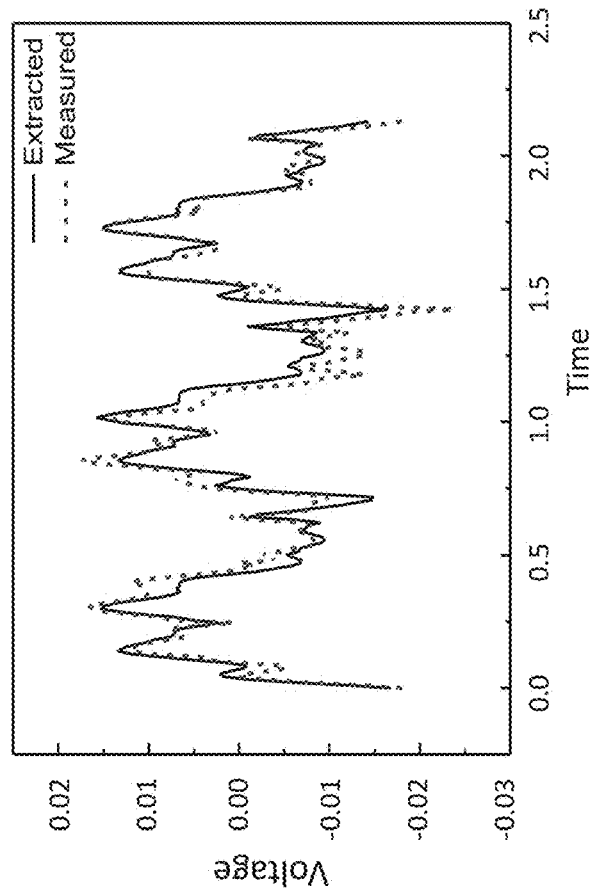

Additionally, as discussed, above, by placing the piezoelectric transducer atop the heart location in the body, the system and method described allow for generating and constructing a heartbeat signal from the respiration signal. FIG. 11A shows the positioning of the piezoelectric sensor in this embodiment to be at the left front surface of the chest on the fourth rib of the thorax atop the area where the heart is located. FIG. 11B shows the output voltage signal measured by the system, where the subject was asked to breath normally under no physical, physiological or environmental stress for 15 seconds but to take a deep breath in the last respiration cycle. The subject was then asked to hold his breath for the next 5 seconds under the same conditions. In the example described in FIG. 11B, the subject was at rest, under no physiological stress and the data was collected under room temperature with humility and pressure at normal readings. Other physical, physiological and environmental conditions may be applied.

To validate the ability of extracting the full heartbeat cycle for every cycle of the respiration signal, each of the full cycles of respiration in FIG. 11B are presented individually. FIGS. 12A to 12D show in sequence each full cycle of the respiration signal, respectively, in FIG. 11B. For each full cycle, the method described in this disclosure was applied in order to construct the heartbeat signal for each signal of a full respiration cycle. The results are shown in FIGS. 12E to 12H, which represent the heartbeat signal for the respiration cycles in FIGS. 12A to 12D, respectively. The measured initial voltage output signal corresponding to the holding breath signal is superimposed on top of each of the heartbeat signals in FIGS. 12E to 12H for comparison and validation of accuracy.

It may be noted from FIGS. 12E to 12H that the slight differences imprinted in the respiration cycles are translated as differences in the heartbeats impacting the respiration signal at that time period. It is also noted that each of the full respiration cycles in FIGS. 12E, 12F, and 12G have three full heartbeat cycles. However, in FIG. 12H, the full respiration cycle has four heartbeat cycles. This is attributed to the subject taking a deep breath in that cycle. Therefore, the depth of respiration is considered a factor that may affect the outcome heartbeat signal constructed according to the method and system described in this current disclosure since such action directly affects the period of the respiration cycle. It should be noted that the number of heartbeats per a full respiration cycle may vary from one subject to another. So this will affect the number of heartbeats either at normal breathing or when the subject takes deep breaths.

Figure 13:
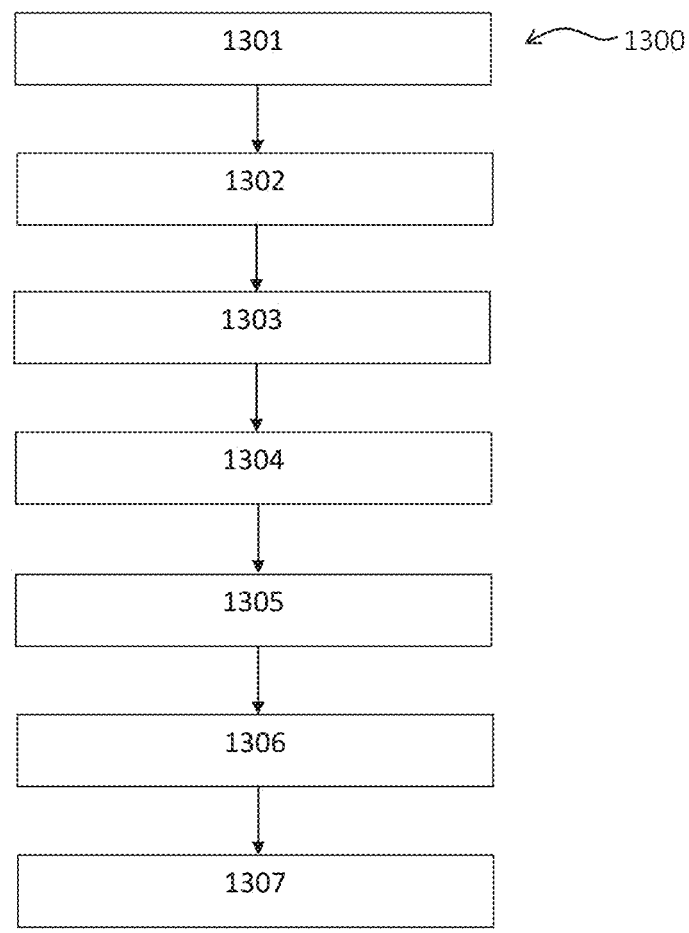
FIG. 13 shows a schematic block diagram representing a method according to an embodiment of the invention.

FIG. 13 shows a schematic block diagram representing the method 1300 implemented in such embodiment. Method 1300 describes an array of piezoelectric sensors generating an electrical signal based on the mechanical movement of the chest of the subject, to which the sensors are attached, where the mechanical movement is due to respiration or cardiac activity while the subject is in a state of holding breath and breathing. Step 1301 describes using the array of sensors to measure an initial voltage output for a respiration signal under certain conditions for a first period and to measure an initial voltage output for a holding breath signal under the same condition for a second period, where the periods reflect the different states. The step also includes storing the initial measured values and the corresponding conditions in a storage device for later access. The step further includes measuring a second voltage output of a second respiration signal for a time other than the first or second period. Step 1302 describes passing the second respiration signal by a processor to a first conditional circuit for amplification. Step 1302 may be skipped if the signal is determined to be above a pre-determined threshold, which is determined based, at least, on the type of the processor and transmitter, and the processor may transmit the signal directly without amplification according to step 1303. The pre-determined threshold value may also be dependent on additional parameters such as age, gender, weight and other physiological, physical or environmental conditions or parameters. Once transmitted, step 1304 shows the signal being received by a receiver system. Once received, step 1305 shows the signal being passed by a second conditioning circuit for amplification. Step 1305 may also be skipped if the received signal is determined to be above a pre-determined threshold. The pre-determined threshold conditions may be the same as or different from the ones identified in step 1302. The signal is then processed by a signal processing unit at step 1306. The receiver and the processor may be at the same location or a location different than the location of the transmitter. At step 1307, the processing unit is used to extract and construct cardiac parameter signals based on the second respiration signal and the initial measured respiration and holding breath signals, according to the method described above. The extracted signals are then assessed remotely according to the method described above.

The method and system described in this disclosure allow for the possibility of continuous monitoring of cardiac activity using a passive, compatible and compact contactless probing system with the ability to model and construct the human cardiac activity signal from the respiration signal without the need to have the subject hold his breath during all measurements. Rather, the subject is required to only hold his breath for a single initial measurement under a certain set of conditions. The subject is then allowed to breath normally under the same conditions after the initial stage and the system and method allow for capturing the respiration signals of the subject and using them to construct the cardiac signal therefrom. This may be achieved because of the light weight characteristic of the piezoelectric material, the wide range of cardiac cycle parameters that may be broadcasted from the transmitter, the receiver system and the ability to remotely process the signal once received. This system and method are simple, reliable and easy to handle as they cause minimal or no inconvenience to the patient, introduce minimal or no limitation to the movement of the patient and provide minimal or no inconvenience to clinics.

The current disclosure describes a system and method for extracting the electrical signal associated with cardiac and lungs activity based on monitoring the respiration activity of the subject and using piezoelectric sensors to transduce mechanical movements due to the respiration activity to electric signals. Once the electrical signal describing the cardiac activity of the subject is extracted, techniques taught in U.S. application Ser. No. 15/095,956 may be used to generate the associate ECG signal with the cardiac electrical activity generated. For example, the ECG signal may be generated using the following equation:

$$EGG(f) = \left[\frac{EGG_o(f)}{Y_{o_R}(f)}\right] Y_R(f) \quad (16)$$

Where $ECG_0(f)$ is the average cycle of single ECG signal in frequency domain taken once and used as long as there are no abnormalities and where ECG (f) represents the ECG signal in the frequency domain. The signal may then be generated in the time domain using inverse Fourier transform.

Interpretation of Terms

Unless the context clearly requires otherwise, throughout the description and the claims:
 "comprise," "comprising," and the like are to be construed in an inclusive sense, as opposed to an exclusive or exhaustive sense; that is to say, in the sense of "including, but not limited to".
 "connected," "coupled," or any variant thereof, means any connection or coupling, either direct or indirect, between two or more elements; the coupling or connection between the elements can be physical, logical, or a combination thereof.
 "herein," "above," "below," and words of similar import, when used to describe this specification shall refer to this specification as a whole and not to any particular portions of this specification.
 "or," in reference to a list of two or more items, covers all of the following interpretations of the word: any of the items in the list, all of the items in the list, and any combination of the items in the list.
 the singular forms "a", "an" and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

Where a component (e.g. a circuit, module, assembly, device, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions and sub-combinations as may reasonably be inferred. The scope of the claims should not be limited by the preferred embodiments set forth in the examples, but should be given the broadest interpretation consistent with the description as a whole.

What is claimed is:

1. A method of using at least one piezoelectric sensor to determining cardiac or lungs activity of a subject based on monitoring breathing activity of the subject and to generate a cardiac electrical signal corresponding to a cardiac parameter, the method comprising:

coupling the at least one piezoelectric sensor to a body part of the subject;

obtaining a first piezoelectric electrical signal from the at least one piezoelectric sensor, the first piezoelectric electrical signal is based on mechanical movement of the body part related to a breathing activity of the subject during a first period and a hold breathing activity of the subject during a second period different from the first period, the first piezoelectric electrical signal is obtained only once for a set of conditions, the first period covers at least one full cycle of breathing activity and the second period covers at least one full cycle of cardiac activity, the breathing activity and the hold breathing activity performed under the set of conditions;

obtaining a second piezoelectric electrical signal from the at least one piezoelectric sensor, the second piezoelectric electrical signal is based on mechanical movement of the body part related to breathing activity of the subject under the set of conditions during a time different from the first period and the second period;

mapping a first part of the first piezoelectric electrical signal corresponding to the at least one full cycle of breathing activity in the first period to a second part of the first piezoelectric electrical signal corresponding to the at least one full cycle of cardiac activity in the second period, the mapping is performed using signal processing techniques, the signal processing techniques comprise transforming the first and second piezoelectric signals into a frequency domain and generating a cardiac electrical signal extraction coefficient representative of the cardiac parameter, the cardiac electrical signal extraction coefficient is based on the first part and the second part of the first piezoelectric electrical signal; and generating solely from the second piezoelectric electrical signals based on the cardiac electrical signal extraction coefficient a first cardiac electrical signal corresponding to the time of the second piezoelectric signal, the first cardiac electrical signal corresponding to the cardiac parameter.

2. A method according to claim 1, where the mapping is performed using a linear one-to-one mapping.

3. A method according to claim 1, the method further comprising storing the cardiac electrical signal extraction coefficient on a memory storage device along with the set of conditions used at the time of obtaining the first and second piezoelectric electrical signals.

4. A method according to claim 3, the method further comprising:

utilizing a new set of conditions selected from a plurality of sets of conditions, each set of conditions in the plurality of sets of conditions is different from one another and from the set of conditions;

obtaining the first piezoelectric electrical signals only once under each one of the new set of conditions to generate a plurality of first piezoelectric electrical signals;

wherein each in the plurality of first piezoelectric electrical signals is obtained independently and separately;

storing in the memory storage device the plurality of first piezoelectric electrical signals independently and separately obtained for the subject, each of the plurality of first piezoelectric electrical signals is based on mechanical movement of the body part related to a respective breathing activity of the subject during a respective first period and a respective hold breathing activity of the subject during a respective second period different from the respective first period under a corresponding set of conditions among the plurality of sets of conditions, wherein the plurality of sets of conditions relate to any combination of physical, physiological and environmental conditions under which the plurality of first piezoelectric signals are obtained separately and independently.

5. A method according to claim 4, wherein the method further comprises:

comparing at least one full cycle in the first cardiac electrical signal to at least one full cycle in each of the plurality of first piezoelectric electrical signals in the respective second period; and assessing whether the subject has a cardiac activity abnormality based on the comparison.

6. A method according to claim 4, wherein the method further comprises:

comparing at least one full cycle in the second piezoelectric electrical signal to at least one full cycle in each of the plurality of first piezoelectric electrical signals in the respective first period; and assessing whether the subject has at least one of a respiratory or cardiac activity abnormality based on the comparison.

7. A method according to claim 1, wherein generating the first cardiac electrical signal comprises one of:

convolving the second piezoelectric electrical signal obtained in a time domain with an inverse Fourier transform of the cardiac electrical signal extraction coefficient; and obtaining an inverse Fourier transform of the product of the cardiac electrical signal extraction coefficient with the second piezoelectric signal in a frequency domain.

8. A method according to claim 7, wherein obtaining the second piezoelectric electrical signal comprises continuously obtaining additional piezoelectric electrical signals different from the first piezoelectric electrical signal, the additional piezoelectric electrical signals are obtained individually and sequentially after the first piezoelectric electrical signal, the additional piezoelectric electrical signals are based on additional mechanical movement of the body part related to the breathing activity of the subject under the set of conditions; and wherein additional cardiac electrical signals are generated solely from the corresponding additional piezoelectric electrical signals;

the method further comprises:

determining at least one cycle in each of the additional cardiac electric signals and comparing the determined at least one cycle with the at least one full cycle of the cardiac activity, respectively, in the second period; and continuously assessing a health condition of the subject based on the comparison.

9. A method according to claim 8, the method further comprises notifying at least one of the subject and a third party of the health condition of the subject.

10. A method according to claim 1, wherein obtaining the first piezoelectric electrical signal is performed when the subject is in good health condition.

11. A method according to claim 10, the method further comprises:
determining a section of the first cardiac electrical signal corresponding to a single cardiac activity cycle and comparing the section with one cycle of the at least one full cycle of cardiac activity obtained in the second period; and assessing a health condition of the subject based on the comparison, wherein assessing the health condition of the subject comprises assessing the subject to have a positive condition or a negative condition.

12. A method according to claim 11, wherein the subject is assessed to have the positive condition when the determined section of the first cardiac electrical signal and the one cycle of the at least one full cycle of cardiac activity obtained in the second period have a correlation value higher than a pre-determined value; and
wherein the subject is assessed to have the negative condition when the determined section of the first cardiac electrical signal and the one cycle of the at least one full cardiac activity cycle obtained in the second period have a correlation value lower than the pre-determined value.

13. A method according to claim 12, the method further comprising: notifying at least one of the subject and a third party of the positive or negative condition.

14. A method according to claim 10, the method further comprises:
determining a section of the second piezoelectric electrical signal corresponding to a single breathing activity cycle and comparing the section with one cycle of the at least one full cycle of breathing activity obtained in the first period; and assessing abnormalities in the subject's cardiac or lung activity based on the comparison.

15. A method according to claim 1, wherein the cardiac parameter is one of Aortic Pressure AP, Left Ventricle Pressure LVP, Left Atrial Pressure LAP, Left Ventricular Volume LV Vol, and heart sounds.

16. A method according to claim 1, the method further comprises positioning the at least one piezoelectric sensor at any one of the subject's left upper body section, right upper body section or any part of the subject's lower body section, wherein the positioning of the at least one piezoelectric sensor allows the subject to move freely without obstruction or limitation.

17. A method according to claim 1, wherein the method further comprises:
wirelessly transmitting the first and second piezoelectric electrical signals using a transmitter; and
receiving the transmitted first and second piezoelectric electrical signals using a receiver located at a location away from the transmitter,
wherein generating solely from the second piezoelectric electrical signals based on the cardiac electrical signal extraction coefficient the first cardiac electrical signal is performed at the location of the receiver.

18. A method according to claim 17, wherein the method further comprises:
comparing each of the first and second piezoelectric electrical signals to a corresponding pre-determined threshold before transmitting each by the transmitter and before transmitting, amplifying any of the first and second piezoelectric electrical signal if any of the first and second piezoelectric electrical signals is determined to be below the corresponding pre-determined threshold; and
comparing each of the first and second piezoelectric electrical signals to the corresponding pre-determined threshold after receiving each by the receiver and after receiving by the receiver, amplifying any of the first and second piezoelectric electrical signals if any of the first and second piezoelectric electrical signals is determined to be below the corresponding pre-determined threshold.

19. A system for determining cardiac or lungs activity of a subject based on monitoring breathing activity of the subject and generating a cardiac electrical signal corresponding to a cardiac parameter, the system comprising:
at least one piezoelectric sensor couplable to a body part of the subject; the at least one piezoelectric sensor for obtaining a first piezoelectric electrical signal, the first piezoelectric electrical signal is based on mechanical movement of the body part related to a breathing activity of the subject during a first period and a hold breathing activity of the subject during a second period different from the first period, the first piezoelectric electrical signal is obtained only once for a set of conditions, the first period covers at least one full cycle of breathing activity and the second period covers at least one full cycle of cardiac activity, the breathing activity and the hold breathing activity performed under the set of conditions; the at least one piezoelectric sensor is also for obtaining a second piezoelectric electrical signal, the second piezoelectric electrical signal is based on mechanical movement of the body part related to breathing activity of the subject under the set of conditions during a time different from the first period and the second period; and
a processor in electrical communication with the at least one piezoelectric sensor, the processor configured to:
receive the first and second piezoelectric electrical signals from the at least one piezoelectric sensor;
obtaining a second piezoelectric electrical signal from the at least one piezoelectric sensor, the second piezoelectric electrical signal is based on mechanical movement of the body part related to breathing activity of the subject under the set of conditions during a time different from the first period and the second period;
use signal processing techniques to map a first part of the first piezoelectric electrical signal corresponding to the at least one full cycle of the breathing activity in the first period to a second part of the first piezoelectric electrical signal corresponding to the at least one full cycle of the cardiac activity in the second period, the signal processing techniques comprise transforming the first and second piezoelectric signals into a frequency domain and generating a cardiac electrical signal extraction coefficient representative of the cardiac parameter, the cardiac electrical signal extraction coefficient is based on the first part and the second part of the first piezoelectric electrical signal; and generate solely from the second piezoelectric electrical signals based on the cardiac electrical signal extraction coefficient a first cardiac electrical signal corresponding to the time of the second piezoelectric signal, the first cardiac electrical signal corresponding to the cardiac parameter.

\* \* \* \* \*